US008257695B2

(12) United States Patent
Rautonen et al.

(10) Patent No.: US 8,257,695 B2
(45) Date of Patent: Sep. 4, 2012

(54) METHOD FOR MODULATING SATIETY SIGNALING WITH SPECIFIC STRAINS OF LACTOBACILLUS ACIDOPHILUS AND BACILLUS

(75) Inventors: Nina Rautonen, Espoo (FI); Heli Putaala, Upinniemi (FI); Arthur Ouwehand, Inkoo (FI); Kirsti Tiihonen, Helsinki (FI); Marta Korczynska, Wageningen (NL); Wouter Herman Noordman, Ede (NL)

(73) Assignee: DuPont Nutrition Biosciences ApS, Copenhagen (DK)

( * ) Notice: Subject to any disclaimer, the term of this patent is extended or adjusted under 35 U.S.C. 154(b) by 558 days.

(21) Appl. No.: 12/162,160

(22) PCT Filed: Jan. 28, 2007

(86) PCT No.: PCT/IB2007/001186
§ 371 (c)(1),
(2), (4) Date: Sep. 18, 2008

(87) PCT Pub. No.: WO2007/085970
PCT Pub. Date: Aug. 2, 2007

(65) Prior Publication Data
US 2010/0061967 A1    Mar. 11, 2010

Related U.S. Application Data

(60) Provisional application No. 60/762,491, filed on Jan. 27, 2006.

(51) Int. Cl.
*A61K 35/74* (2006.01)
(52) U.S. Cl. ............... 424/93.45; 435/252.9; 435/29; 530/350
(58) Field of Classification Search .................. None
See application file for complete search history.

(56) References Cited

U.S. PATENT DOCUMENTS

| 5,578,302 A | 11/1996 | Brassart et al. |
| 2005/0186189 A1 | 8/2005 | Hsu et al. |

FOREIGN PATENT DOCUMENTS

| JP | 2001-292728 | 10/2001 |
| WO | WO 01/88095 A1 | 11/2001 |
| WO | WO 02/38165 A1 | 5/2002 |
| WO | WO 2004/014403 A1 | 2/2004 |
| WO | WO 2006/025643 A1 | 3/2006 |
| WO | WO 2006/052135 A2 | 5/2006 |
| WO | WO 2007/043933 A1 | 4/2007 |

OTHER PUBLICATIONS

Ali, Ali, A., et al., "Effects of probiotics and isoflavones on metabolic parameters in a genetic model of obesity and diabetes," *FASEB Journal* (2002) vol. 16:5.

Backhed, Fredrik, et al., "Host-bacterial mutualism in the human intestine," *Science* (2005) vol. 307 pp. 1915-1920.
Backhed, Fredrik, et al., "The gut microbiota as an environmental factor that regulates fat storage," *PNAS* (2004) vol. 101:44 pp. 15710-15723.
Bleau, C., et al., "New *Lactobacillus acidophilus* isolates reduce the release of leptin by murine adipocytes leading to lower interferon-gamma production," *Clinical and Experimental Immunology* (2005) vol. 140:3 pp. 427-435.
Fosset, Spohie, et al., "Pharmacokinetics and feeding responses to muramyl dipeptide in rats," *Physiolgoy & Behavior* (2003) vol. 79 pp. 173-182.
Gee, Jennifer M., et al., "Dietary lactitol fermentation increases circulating peptide YY and glucagon-like peptide-1 in rats and humans," *Nutrition* (2005) vol. 21:10 pp. 1036-1043.
Korbonits, M., et al., "Ghrelin and cannabinoid interactions on food intake," *Endocrine* (2005) (Abstract Only).
Le Roux, C.W., et al., "Attenuated peptide YY release in obese subjects is associated with reduced satiety," *Endocrinology* (2005) pp. 1-22.
Lee, Hui-Young, et al., "Human originated bacteria, *Lactobacillus rhamnosus* PL60, produce conjugated linoleic acid and show anti-obesity effects in diet-induced obese mice," *Biochimica and Biophysica Acta* (2006) vol. 1761:7 pp. 736-744.
Ley, Ruth E., et al., "Obesity alters gut microbial ecology," *PNAS* (2005) vol. 102:31, pp. 11070-11075.
Livak, Kenneth J., et al., "Analysis of relative gene expression data using real-time quantitative PCR and the $2^{-\Delta\Delta C}$ T method," *Methods* (2001) vol. 25 pp. 402-408.
Naruszewcz, Marek, et al., "Effect of *Lactobacillus plantarum* 299v on cardiovascular disease risk factors in smokers," *American Journal of Clinical Nutrition* (2002) vol. 76:6, pp. 1249-1255.
Renshaw, D., et al., "Peptide YY: A potential therapy for obesity," *Current Drug Targets* (2005) vol. 6:2, pp. 171-179 (Abstract Only).
Roberfroid, Marcel B., "Prebiotics and probiotics: are they functional foods?," *American Journal of Clinical Nutrition* (2000) vol. 71, pp. 1682S-1687S.
Schaffer, Amanda, "Someday, there will be a fat pill," (Apr. 26, 2005), Available: www.slate.com/id/2117332/ (Accessed: Jan. 1, 2006).
Stanely, Sarah, et al., "Hormonal regulation of food intake," *Physiol Rev* (2005) vol. 85, pp. 1131-1158.
Stock, Sue, et al., "Ghrelin, PYY, GP and hunger responses to a mixed meal in anorexic, obese and control female adolescents," *Journal of Clinical Endocrinology & Metabolism* (2005) pp. 1-36.
Tovar, Sulay A., et al., "Regulation of peptide YY levels by age hormonal, and nutritional status," *Obesity Research* (2004) vol. 12:12 pp. 1944-1950.

(Continued)

*Primary Examiner* — Hope Robinson
(74) *Attorney, Agent, or Firm* — Steptoe & Johnson LLP

(57) ABSTRACT

Use of at least one strain of a microorganism and/or a metabolite thereof in the manufacture of a support for administration to a subject for modulating satiety signalling, wherein the support is a pharmaceutically acceptable support or a food product. Suitably, the at least one strain of a microorganism and/or a metabolite thereof may be administered to the subject for the treatment and/or prevention of excess weight and/or a disease caused by excess weight. Likewise, the at least one strain of a microorganism and/or a metabolite thereof is administered to the subject for the treatment and/or prevention of obesity and/or a caused by obesity. Preferably, the microorganism is a probiotic microorganism. Suitably the microorganism may be a lactic acid bacterium. Li one embodiment the microorganism is a strain of *Lactobacillus* spp. and/or *Bifidobacterium* spp., for example a strain of *Lactobacillus acidophilus, L. curvatus, L. salivarius* and/or *B. lactis*.

15 Claims, 7 Drawing Sheets

OTHER PUBLICATIONS

Adams, V.C., et al., "Ghrelin and cannabinoids increase food intake via stimulation of hypothalamic amp-activated protein kinase (AMPK)," *Endocrine* (2005) (Abstract only).

Vickers, S.P., et al., "Cannabinoids and the regulation of ingestive behavior," *Current Drug Targets* (2005) vol. 6:2, pp. 215-223 (Abstract Only).

Wu, Ming-Shiang, et al., "A case-control study of association of *Helicobacter pylori* infection with morbid obesity in Taiwan," *Arch Intern Med.* (2005) vol. 165, pp. 1552-1555.

Yadav, Hariom, et al., "Antidiaberic effects of probiotic dahi containing *Lactobacillus acidophilus* and *Lactobacillus casei* in high fructose fed rats," *Nutrition* (2007) vol. 23:1, pp. 62-68.

METHOD FOR MODULATING SATIETY SIGNALING WITH SPECIFIC STRAINS OF *LACTOBACILLUS ACIDOPHILUS* AND *BACILLUS*

CLAIM OF PRIORITY

This application claims priority under 35 USC 371 to International Application No. PCT/IB2007/001186, filed on Jan. 26, 2007, which claims priority to U.S. Provisional Application Ser. No. 60/762,491, filed Jan. 27, 2006, each of which is incorporated by reference in its entirety.

FIELD OF INVENTION

The present invention relates to satiety of appetite.

In one embodiment the present invention relates to the use of at least one strain of a microorganism, preferably a lactic acid bacterium, preferably a probiotic bacterium, such as *Lactobacillus* spp. (for example *L. acidophilus, L. salivarius* and/or *L. curvatus*) and/or *Bifidobacterium* spp. (such as *B. lactis*), to prepare a support administered to humans or animals for modulating satiety signalling, preferably inducing satiety.

The present invention yet further relates to the use of at least one strain of a microorganism, preferably a lactic acid bacterium, preferably a probiotic bacterium, such as *Lactobacillus* spp. (for example *L. acidophilus, L. salivarius* and/or *L. curvatus*) and/or *Bifidobacterium* spp. (such as *B. lactis*), in the treatment or reduction or management of excess weight and/or in the treatment of diseases caused by being overweight, particularly in the treatment of obesity, and/or obesity related diseases.

TECHNICAL BACKGROUND

Dieting and weight loss for aesthetic (cosmetic) reasons is practised by individuals throughout the world. Scientists, drug developers and food developers have over the past decade introduced a variety of appetite suppressants and/or weight loss drugs and/or "healthy" food ranges in order to assist dieters in their plight to shed the weight.

Dieting is not restricted to humans, but includes other animals, with diet plans for pets being common.

From an evolutionary perspective animals (including humans) have adapted to gorge food and store energy in case of famine. Unfortunately, however, although this was useful in times when food was scarce, now in times where it is possible to constantly eat this can lead to overweight and, in some cases, obesity.

Obesity has become a major public health problem. Health conditions caused or exacerbated by obesity include hypertension, diabetes mellitus, sleep apnea, obesity-related hypoventilation, back and joint problems, cardiovascular disease, non-alcoholic fatty liver disease and gastroesophageal reflux disease.

The body mass index (BMI) (calculated as weight in kilograms divided by the square of height in meters) is the most commonly accepted measurement for overweight and/or obesity. A BMI exceeding 25 is considered overweight, while obesity is defined as a BMI of 30 or more, with a BMI of 35 or more considered as serious comorbidity and a BMI of 40 or more considered morbid obesity.

Obestatin is a peptide hormone that is produced in the cells lining the stomach and small intestine of several mammals including humans; it drastically reduces appetite in mice and is expected to do the same in humans.

Surprisingly, obestatin is encoded by the same gene that also encodes ghrelin, a peptide hormone that increases appetite. Ghrelin and obestatin are both derived from a prohormone produced by the same gene and are divided by post-translational processing. The purpose of this mechanism remains unclear, however it explains earlier findings, namely that removing the ghrelin gene from mice did not significantly reduce their appetite.

Obestatin has been considered for use as a drug against obesity, however it would have to be delivered as a nasal spray or by injection, as the peptide is destroyed by gastric juices.

There are currently few treatments for obesity. Of the two drugs approved for use in the US Roche's Xenical™ (which blocks the digestion of fat) is relatively effective at promoting weight loss, but has some unpleasant side-effects. The other drug approved for use in the US is Abbot Laboratories' Meridia™, which has allegedly been proven to be not particularly effective (Schaffer A. www.slate.com/id/2117332, 26 Apr. 2005).

One experimental drug currently in trials is Rimonabant™ (a cannabinoid receptor antagonist) which allegedly stems cravings in humans, thus reducing obese patients' appetites.

There therefore is a need for an effective tool for reducing weight, preventing weight gain, facilitating weight loss and/or treating obesity.

Among microorganisms, in particular among bacteria, some have a positive influence on the immune system, in particular the lactic acid bacteria and bifidobacteria, and are described as "probiotic" bacteria or strains.

Generally, by probiotic bacterium or strain it is meant a non-pathogenic microorganism which, when ingested live, exercises a beneficial effect on the host's health or physiology. These probiotic strains generally have the ability to survive the passage through the upper part of the digestive tract. They are non-pathogenic, non-toxic and exercise their beneficial effect on health on the one hand via ecological interactions with the resident flora in the digestive tract, and on the other hand via their ability to influence the immune system in a positive manner via the "GALT" (gut-associated lymphoid tissue). Depending on the definition of probiotics, these bacteria, when given in a sufficient number, have the ability to progress live through the intestine, however they do not cross the intestinal barrier and their primary effects are therefore induced in the lumen and/or the wall of the gastrointestinal tract. They then form part of the resident flora during the administration period. This colonization (or transient colonization) allows the probiotic bacteria to exercise a beneficial effect, such as the repression of potentially pathogenic microorganisms present in the flora and interactions with the immune system of the intestine.

The probiotic strains most commonly used, in particular in dairy products, are principally bacteria and yeasts of the following genera: *Lactobacillus* spp., *Streptococcus* spp., *Enterococcus* spp., *Bifidobacterium* spp. and *Saccharomyces* spp.

Among the probiotic effects recorded for these bacteria, there can be mentioned for example the improvement of lactose tolerance, enhancement of immune function, prevention or treatment of gastrointestinal and urogenital infections and reduction of the cancer risk.

SUMMARY ASPECTS

A seminal finding of the present invention is that microorganisms, in particular lactic acid bacteria and/or probiotic microorganisms and/or probiotic lactic acid bacteria, and/or a metabolite thereof according to the present invention induces satiety, in particular postprandial satiety, in a subject.

In particular, a seminal finding of the present invention is that lactic acid bacteria (such as *Lactobacillus acidophilus*, for example strain PTA-4797; *Lactobacillus curvatus; Lactobacillus salivarius;* and/or *Bifidobacterium lactis*) and/or a metabolite thereof induces satiety, in particular postprandial satiety, in a subject.

DETAILED ASPECTS

The detailed aspects of this invention are detailed below. In part some of the detailed aspects are discussed in separate sections. This is for ease of reference and is in no way limiting.

In one aspect, the present invention provides the use of at least one strain of a microorganism and/or a metabolite thereof for administration to a subject for modulating satiety signalling (for example, in the intestine).

In one aspect, the present invention provides the use of at least one strain of a microorganism and/or a metabolite thereof in the manufacture of a support for administration to a subject for modulating satiety signalling (for example, in the intestine).

The term "modulating satiety signalling" as used herein refers to varying the amplitude and/or frequency of neural and/or endocrine signalling associated with satiety.

In some embodiments, "modulating satiety signalling" refers to varying the amplitude and/or frequency of satiety markers.

The term "satiety" as used herein means the state of being satiated or glutted of appetite, i.e. fullness beyond desire or being fully satisfied.

In a further aspect, the present invention provides the use of at least one strain of a microorganism and/or a metabolite thereof in the manufacture of a support for administration to a subject for inducing satiety.

In another aspect, the present invention provides the use of at least one strain of a microorganism and/or a metabolite thereof in the manufacture of a medicament for the treatment and/or prevention of excess weight, including obesity, and/or a disease or disorder caused by excess weight, including an obesity related disease or disorder.

In yet another aspect, the present invention provides a method of modulating satiety signalling (for example, in the intestine) in a subject which method comprises administering to the subject an effective amount of at least one strain of a microorganism and/or a metabolite thereof In a further aspect, the present invention provides a method of inducing satiety in a subject which method comprises administering to the subject an effective amount of at least one strain of a microorganism and/or a metabolite thereof.

In a yet further aspect, the present invention provides a method of treating and/or preventing excess weight, including obesity, and/or a disease or disorder caused by excess weight, including an obesity related disease in a subject, which method comprises administering to the subject an effective amount of at least one strain of a microorganism and/or a metabolite thereof.

In a further aspect, the present invention provides a cosmetic method of reducing excess weight in a non-obese subject, which method comprises administering to the subject an effective amount of at least one strain of a microorganism and/or a metabolite thereof.

In another embodiment, the present invention provides a cosmetic use of at least one strain of a microorganism and/or a metabolite thereof in the manufacture of a support for administration to a non-obese subject for inducing satiety.

In a further embodiment, the present invention provides a method for selecting a microorganism and/or a metabolite thereof for administration to a subject for inducing satiety and/or treating excess weight, including obesity, wherein the method comprises the steps of:
   a) bringing a microorganism and/or a metabolite thereof into contact with at least one epithelial cell,
   b) detecting the expression of a satiety marker (such as protein tyrosine tyrosine (PYY)) in at least one epithelial cell.

In a further embodiment, the present invention provides a method for selecting a microorganism and/or a metabolite thereof to prepare a support for administration to a subject for inducing satiety and/or treating excess weight, including obesity, wherein the method comprises the steps of:
   a) bringing a microorganism and/or a metabolite thereof into contact with at least one epithelial cell,
   b) detecting the expression of a satiety marker (such as protein tyrosine tyrosine (PYY)) in at least one epithelial cell.

The epithelial cell or cells used during stages a) or b) preferably come from Caco-2 cell line. This is a cancer colon cell line. They can also be isolated and purified cells from biopsies of items from operations on humans. Caco-2 cells are publicly available in a number of cell line catalogues, such as from the ATCC (American Type Culture Collection) with a number HTB-37, for example.

Stage a) is carried out preferably using from 1 to 100 microorganism cells per one epithelial cells to be tested with at least one epithelial cell.

The contact period, during stage a), can vary from 0 hour to 24 hours, and is preferably about 3 hours or at least 3 hours.

Generally, the bringing into contact with the cells according to stage a) is carried out under standard temperature, modified-atmospheres and sterility conditions well known to a person skilled in the art, in particular under in vitro epithelial cell culture conditions.

Stage b) of the selection process according to the invention is carried out by preferably detecting the expression, and optionally its level, of the messenger RNA of the satiety marker (such as PYY), for example by PCR inter alia by quantitative PCR or by immunohistochemistry or by radio-immunoassay. Other techniques well known to a person skilled in the art for the detection of mRNA and its measurement can be used.

For some embodiments, the microorganism in accordance with the present invention may be viable.

For some embodiments, the microorganism in accordance with the present invention may be dead or non-viable.

Without wishing to be bound by theory, it is believed that the metabolites, for example the soluble metabolites, associated with, for example produced by, the microorganism may be causing the advantageous effect of the microorganism. For some aspects, it is therefore unnecessary for the microorganism cells to be in direct contact with the target cells.

For some aspects, it is believed that one or more metabolites associated with, for example produced by, the microorganism may be suitable for achieving the beneficial effects taught herein. In such instances, it may be unnecessary to include the microorganisms themselves.

The term "metabolite thereof" as used herein means one or more compounds either extracted from the microorganism according to the present invention or obtained from a culture medium in which a microorganism according to the present invention is or was cultured. In some aspects the metabolite may be a crude extract of the culture medium and/or microorganism. Suitably, for some aspects the metabolite may be one or more compounds isolated and/or purified from the culture medium and/or the microorganism.

In some embodiments suitably the metabolite may be a soluble metabolite.

In some embodiments the metabolite may be a water soluble metabolite.

In some embodiments the metabolite may be a lipid soluble metabolite.

Suitably, the metabolite may be a metabolite which is present in the supernatant phase isolated from a culture of the microorganism using the methodology as taught in U.S. Pat. No. 5,578,302 and/or in accordance with the examples taught herein In one embodiment, the metabolite may be obtainable (preferably obtained) by culturing a bacterium (preferably a lactic acid bacterium, preferably a probiotic bacterium, such as *Lactobacillus* spp. (for example *L. acidophilus, L. salivarius* and/or *L. curvatus*) or *Bifidobacterium* spp. (such as *B. lactis*)) in a culture medium until the OD of the culture at λ600 reaches at least 0.6, preferably 0.6 to 1.5; removing the bacteria by centrifugation and/or filtration (such as, for example, centrifugation at 25° C., 5 min, 3000 g and/or sterile-filtration) to result in a filtrate comprising said metabolite(s).

Suitably, the metabolite(s) is obtainable (preferably obtained) using an MRS culture medium either with 1.0% sugar or without sugar. Suitably, the metabolite(s) is obtainable (preferably obtained) by culturing the bacteria at 37° C. Suitably, the metabolite(s) is obtainable (preferably obtained) by culturing the bacteria anaerobically.

In in vitro assays the metabolite in the form of the filtrate may optionally be admixed with tissue culture cells in a tissue culture medium. Preferably, the filtrate containing the metabolite(s) is admixed with the tissue culture medium such that the filtrate/tissue culture medium mixture comprises at least 10% v/v filtrate and at most 90% v/v tissue culture medium.

When the metabolite(s) is loaded onto a support, preferably filtrate/support mixture ratio is 1:10 or greater.

Suitably, the microorganism in accordance with the present invention may be co-cultured with one or more target cells thus allowing the transfer of soluble fractions.

Suitably, the microorganism may not be in cell to cell contact with the target cell(s).

Suitably, the microorganism according to the present invention or the metabolite thereof may be in the form of a bacterial suspension, before or after freezing, in the form or concentrates, either in dry, lyophilized or frozen form. Whatever the form used, the strain can be frozen.

Suitably, the microorganism and/or metabolite thereof according to the present invention may contain different additives. Suitably additives may be added during its drying and/or during its lyophilization.

The microorganism used in accordance with the present invention, (such as a strain of *Lactobacillus* spp.; for example a strain of *Lactobacillus acidophilus, L. salivarius* and/or *Lactobacillus curvatus* and/or a strain of *Bifidobacterium*, for example *B. lactis*), may comprise from $10^6$ to $10^{12}$ CFU of bacteria/g of support, and more particularly from $10^8$ to $10^{12}$ CFU of bacteria/g of support, preferably $10^9$ to $10^{12}$ CFU/g for the lyophilized form.

Suitably the microorganism used in accordance with the present invention, (such as a strain of *Lactobacillus* spp.; for example a strain of *Lactobacillus acidophilus, L. salivarius* and/or *Lactobacillus curvatus* and/or a strain of *Bifidobacterium*, for example *B. lactis*), may be administered at a dosage of from about $10^6$ to about $10^{12}$ CFU of microorganism/dose, preferably about $10^8$ to about $10^{12}$ CFU of microorganism/dose. By the term "per dose" it is meant that this amount of microorganism is provided to a subject either per day or per intake, preferably per day. For example, if the microorganism is to be administered in a food support (for example in a yoghurt)—then the yoghurt will preferably contain from about $10^8$ to $10^{12}$ CFU of the microorganism. Alternatively, however, this amount of microorganism may be split into multiple administrations each consisting of a smaller amount of microbial loading—so long as the overall amount of microorganism received by the subject in any specific time (for instance each 24 h period) is from about $10^6$ to about $10^{12}$ CFU of microorganism, preferably $10^8$ to about $10^{12}$ CFU of microorganism.

In accordance with the present invention an effective amount of at least one strain of a microorganism may be at least $10^6$ CFU of microorganism/dose, preferably from about $10^6$ to about $10^{12}$ CFU of microorganism/dose, preferably about $10^8$ to about $10^{12}$ CFU of microorganism/dose.

In one embodiment, preferably the microorganism used in accordance with the present invention, (such as a strain of *Lactobacillus* spp.; for example a strain of *Lactobacillus acidophilus, L. salivarius* and/or *Lactobacillus curvatus* and/or a strain of *Bifidobacterium*, for example *B. lactis*) may be administered at a dosage of from about $10^6$ to about $10^{12}$ CFU of microorganism/day, preferably about $10^8$ to about $10^{12}$ CFU of microorganism/day. Hence, the effective amount in this embodiment may be from about $10^6$ to about $10^{12}$ CFU of microorganism/day, preferably about $10^8$ to about $10^{12}$ CFU of microorganism/day.

CFU stands for "colony-forming units". By gram of support is meant preferably the food product or the pharmaceutically acceptable support.

Advantageously, the present invention is an effective tool for reducing weight gain and/or facilitating weight loss and/or treating or preventing obesity and/or treating or alleviating disorders or diseases related to or caused by obesity or being overweight.

Without wishing to be bound by theory the microorganism and/or metabolite thereof may mediate weight loss and/or result in satiety by increasing satiety signalling in the intestine.

Without wishing to be bound by theory the microorganism and/or metabolite may mediate weight loss and/or result in satiety via its effect on a gut hormone and/or on one or more receptors found in the gut.

Some of the peripheral regulators of appetite, including gut hormones, are discussed in Stanley et al Physiol. Review 85: 1131-1158 2005.

Without wishing to be bound by theory the microorganism and/or metabolite thereof may mediate weight loss and/or result in satiety via its effect on a satiety marker (such as the gut hormone Peptide Tyrosine Tyrosine (PYY) for example).

Satiety

The term "satiety" as use herein means the state of being satiated or glutted of appetite, i.e. fullness beyond desire or being fully satisfied.

Suitably, the present invention may be for increasing satiety.

Preferably the present invention is for inducing and/or increasing postprandial satiety.

The person skilled in the art would understand that satiety and post-prandial satiety may be measured in a number of ways.

For example, without wishing to be bound by theory there is a link between the level of satiety marker(s) (such as the gut hormone PYY either in the blood or in the gut) and the level of satiety.

Therefore, satiety and/or post-prandial satiety can be measured by determining the level of one or more satiety markers (for example PYY either in the blood of the subject and/or in the gut of the subject). Suitably the samples may be taken at intervals prior to and at intervals after the subject consumes a specific meal. For example, increased levels of expression of PYY and/or increased levels of PYY may indicate satiety. The relationships between other satiety markers and satiety are known to those of ordinary skill in the art.

In addition, or alternatively, satiety and/or post-prandial satiety may be measured in animal studies by measuring the food intake of the animal and/or the time interval between feeding of the animal and/or the weight of the animal. A reduction in food intake and/or weight of the animal indicates satiety. In addition, or as an alternative, an increase in the time interval between feeding of the animal indicates satiety.

In addition, or alternatively, satiety and/or post-prandial satiety may be measured subjectively by a subject by use of a questionnaire where subjects are asked the following questions: "how hungry are you", "how full are you", "how much can you eat" and "what is your desire to eat". Their perception can be rated from 0 (lowest) to 10 (highest) on a 100 mm visual analog scale (as taught in Stock et al J. of Clinical Endocrinology & Metabolism, first published 18 Jan. 2005 as doi:10.1210/jc.2004.1251). This reference is incorporated herein by reference. The subject is preferably requested to complete the questionnaire at intervals before and at intervals after the subject consumes a specific meal.

In some embodiments satiety may mean one or more of the following:
a) postprandial satiety;
b) a reduction in pre-meal hunger;
c) a strengthening in within meal satiation to reduce meal size; and/or
d) an increase in the between mean state of satiety, which may prevent compensatory increases in meal numbers and/or may reduce between meal snacking.

In some embodiments satiety may be measured as one or more of the following:
i) a reduction in food intake by the subject compared to a comparative test subject and/or compared with the subject pre-treatment;
ii) a reduction in body weight of the subject compared with the subject pre-treatment;
iii) a reduction in adiposity compared to a comparative test subject and/or compared with the subject pre-treatment.

Satiety Marker

The term "satiety marker" as used herein refers to a compound(s) and/or gut hormone(s) involved in the regulation of appetite and/or food intake.

Satiety markers include, but are not limited to, pancreatic polypeptide (PYY), cholecystokinin (CCK), Glucagon-like peptide-1 (GLP-1), insulin, leptin, ghrelin, orexins, orexigenic hypothalamic neuropeptide Y (NPY), acetic acid, amylin, and oxyntomodulin.

In one embodiment, the satiety marker is preferably a gut hormone.

In one embodiment the satiety marker may be one or more of PYY, CCK, GLP-1, insulin, leptin, ghrelin, orexins, orexigenic hypothalamic neuropeptide Y (NPY), amylin or oxyntomodulin.

Suitably, the satiety marker may be selected from any one or more of the following: PYY, CCK, GLP-1 and insulin.

Without wishing to be bound by theory the microorganism and/or metabolite thereof of the present invention may induce satiety by increasing the plasma levels of any one or more of: PYY, CCK, GLP-1 and insulin. The increase is compared with an equivalent control, but which has not been administered the microorganism and/or metabolite thereof.

In one embodiment, the microorganism and/or metabolite thereof of the present invention may induce satiety by increasing the levels of any one or more of the following satiety markers in the gut: PYY, CCK, GLP-1 and insulin. The increase is compared with a control which has not been administered the microorganism and/or metabolite thereof.

Without wishing to be bound by theory the microorganism and/or metabolite thereof of the present invention may induce satiety by increasing the level of leptin in peripheral blood and/or by decreasing the level of leptin in the brain. The increase is compared with a control which has not been administered the microorganism and/or metabolite thereof.

In one embodiment, the microorganism and/or metabolite thereof of the present invention may increase the level of PYY. The increase is compared with a control which has not been administered the microorganism and/or metabolite thereof.

In an alternative or additional embodiment, the microorganism and/or metabolite thereof of the present invention may increase the level of CCK. The increase is compared with a control which has not been administered the microorganism and/or metabolite thereof.

In another embodiment, the microorganism and/or metabolite thereof of the present invention may induce satiety by decreasing the level of one or more gut hormone(s) in the gut and/or in the plasma such as any one or more of the following: ghrelin and orexins. The decrease is compared with a control which has not been administered the microorganism and/or metabolite thereof.

In another embodiment, the satiety marker may be acetic acid. In this embodiment, the microorganism and/or metabolite thereof of the present invention may induce satiety by increasing the level of acetic acid in the blood. The increase is compared with a control which has not been administered the microorganism and/or metabolite thereof.

Support

The support employed during the use according to the present invention is preferably a pharmaceutically acceptable support or a food product. Further information with regard to both foods and pharmaceuticals are given below.

A pharmaceutically acceptable support may be for example a support in the form of compressed tablets, tablets, capsules, ointments, suppositories or drinkable solutions. Other suitable forms are provided below.

Preferably, the support employed during the use according to the invention is a food product such as a food supplement, a drink or a powder based on milk. Preferably it is a dairy product of animal or vegetable origin. As noted further below, here the term "food" is used in its broadest sense—and covers food for humans as well as food for animals (i.e. a feed).

The term "dairy product" as used herein is meant to include a medium comprising milk of animal and/or vegetable origin. As milk of animal origin there can be mentioned cow's, sheep's, goat's or buffalo's milk. As milk of vegetable origin there can be mentioned any fermentable substance of vegetable origin which can be used according to the invention, in particular originating from soybeans, rice or cereals.

Still more preferably the support employed according to the invention is a fermented milk or humanized milk.

Overweight/Obesity

The body mass index (BMI) (calculated as weight in kilograms divided by the square of height in meters) is the most commonly accepted measurement for overweight and/or obesity.

A BMI exceeding 25 is considered overweight.

Obesity is defined as a BMI of 30 or more, with a BMI of 35 or more considered as serious comorbidity and a BMI of 40 or more considered morbid obesity.

The term "obesity" as used herein includes obesity, comorbidity obesity and morbid obesity. Therefore, the term "obesity" as used here may be defined as a subject having a BMI of more than or equal to 30.

In some embodiments, suitably an obese subject may have a BMI of more than or equal to 30, suitably 35, suitably 40.

The term "excess weight" as used herein means the excess weight of the subject. The term "excess weight" as used herein means that that the subject is considered overweight. There term "overweight" as used herein means that the subject has a BMI exceeding 25.

Excess weight and/or obesity may be measured using the BMI. Therefore a reduction in excess weight and/or obesity may be measured using the BMI.

A reduction in excess weight and/or obesity may also (or alternatively) be measured simply by measuring the weight of the subject relative to a control and/or before and after administration of the microorganisms and/or metabolite thereof according to the present invention.

Without wishing to be bound by theory, there may also be a link between serum or blood inflammatory markers (such as C-reactive protein and/or interleukin 6 and/or TNF-RII for example) and obesity. In addition, there may also be a correlation between serum or blood inflammatory markers and BMI. Hence, in one embodiment one may measure blood inflammatory markers to determine obesity and/or a reduction in obesity in a subject.

Disorders/Diseases Related to or Caused by Excess Weight and/or Obesity

Health conditions (i.e. disorders and/or diseases) caused or exacerbated by obesity include hypertension, diabetes mellitus, for example type-2 diabetes, sleep apnea, obesity-related hypoventilation, back and joint problems, cardiovascular disease, non-alcoholic fatty liver disease and gastroesophageal reflux disease.

Subject

The term "subject", as used herein, means an animal. Preferably, the subject is a mammal, including for example livestock (including cattle, horses, pigs, chickens and sheep), and humans. In some aspects of the present invention the animal is a companion animal (including pets), such as a dog or a cat for instance. In some aspects of the present invention, the subject may suitably be a human.

Medicament

The term "medicament" as used herein encompasses medicaments for both human and animal usage in human and veterinary medicine. In addition, the term "medicament" as used herein means any substance which provides a therapeutic and/or beneficial effect. The term "medicament" as used herein is not necessarily limited to substances which need Marketing Approval, but may include substances which can be used in cosmetics, nutraceuticals, food (including feeds and beverages for example), probiotic cultures, and natural remedies. In addition, the term "medicament" as used herein encompasses a product designed for incorporation in animal feed, for example livestock feed and/or pet food.

Treatment

It is to be appreciated that all references herein to treatment include curative, palliative and prophylactic treatment.

Substantially Pure Form and/or Isolated Form

For some aspects the microorganism and/or metabolite according to the present invention may be in a substantially pure form or may be in an isolated form.

The term "substantially pure form" is used to indicate that the microorganism and/or metabolite according to the present invention is present at a high level. When the microorganism and/or metabolite is in a substantially pure form, the microorganism and/or metabolite is desirably the predominant component present in a composition. Preferably it is present at a level of more than 30%, of more than 50%, of more than 75%, of more than 90%, or even of more than 95%, said level being determined on a dry weight/dry weight basis with respect to the total composition under consideration.

At very high levels (e.g. at levels of more than 90%, of more than 95% or of more than 99%) the component may be regarded as being "isolated". Biologically active substances of the present invention (including polypeptides, nucleic acid molecules, carbohydrates identified/identifiable via screening, lipids identified/identifiable via screening, moieties identified/identifiable via screening, etc.) may be provided in a form that is substantially free of one or more contaminants with which the substance might otherwise be associated. Thus, for example, they may be substantially free of one or more potentially contaminating polypeptides and/or nucleic acid molecules.

They may be provided in a form that is substantially free of other cell components (e.g. of cell membranes, of cytoplasm, etc.). When a composition is substantially free of a given contaminant, the contaminant will be at a low level (e.g. at a level of less than 10%, less than 5% or less than 1% on the dry weight/dry weight basis set out above).

Microorganism

Suitable viable microorganisms for use in the present invention include bacteria, moulds and/or yeasts.

Preferably, the viable microorganisms for use in the present invention are viable bacteria.

The term "viable micro-organism" means a microorganism which is metabolically active.

The microorganism may be a naturally occurring microorganism or it may be a transformed microorganism. The microorganism may also be a combination of suitable microorganisms.

In some aspects, the microorganism according to the present invention may be one or more of the following: a bacterium, a fungus, a yeast.

Suitably, the microorganism according to the present invention may be a bacterium.

Suitably, the microorganism according to the present invention may be a bacterium from one or more of the following genera: *Lactococcus, Streptococcus, Pediococcus, Enterococcus, Leuconostoc, Carnobacterium, Propionibacterium, Bifidobacterium* and *Lactobacillus*.

Preferably, in some embodiments, the microorganism according to the present invention is a probiotic microorganism. Suitably, the probiotic microorganism may be a bacterium or yeast from the following genera: *Lactobacillus* spp., *Streptococcus* spp., *Enterococcus* spp., *Bifidobacterium* spp. and *Sacharomyces* spp.

For some embodiments, the microorganism according to the present invention may be a lactic acid bacterium. Suitably the lactic acid bacterium may be one from the following genera: *Lactobacillus, Streptococcus, Lactococcus, Leu-* conostoc, *Carnobacterium, Enterococcus, Brevibacterium*, and *Vagococcus*. This list is not exhaustive.

For some embodiments, the microorganism according to the present invention is a probiotic lactic acid bacterium. A probiotic lactic acid bacterium may be one from the following genera: *Lactobacillus* spp., *Bifidobacterium* spp., *Streptococcus* spp., and *Enterococcus* spp.

Other genera of bacteria which may be used in accordance with the present invention include: *Pediococcus, Micrococcus, Staphylococcus, Bacillus, Kocuria, Arthrobacter, Proprionibacterium, Brevibacterium* and *Corynebacterium*.

Preferably the microorganism to be used in accordance with the present invention is a microorganism which is generally recognised as safe and, which is preferably GRAS approved.

A skilled person will readily be aware of specific species and or strains of microorganisms from within the genera described herein which are used in the food and/or agricultural industries and which are generally considered suitable for human and/or animal consumption.

Preferably, the microorganism used in accordance with the present invention is one which is suitable for human and/or animal consumption.

In one embodiment preferably the microorganism is from the genus *Lactobacillus* or the genus *Bifidobacterium* or is a mixture thereof. Suitably, the microorganism may be a strain from the species *L. acidophilus, L. curvatus, L. rhamnosus, L. casei, L. paracasei, L. salivarius, B. lactis. B animalis, B. longum* and/or *B. bifidum*. In one embodiment, preferably the microorganism may be a strain from the species *L. acidophilus, L. curvatus, L. salivarius* and/or *B. lactis*.

In one embodiment preferably the microorganism is from the genus *Lactobacillus*.

Suitably, the microorganism may be a strain from the species *L. acidophilus, L. curvatus, L. rhamnosus, L. casei, L. paracasei* and *L. salivarius*. In one embodiment, preferably the microorganism may be a strain from the species *L. acidophilus, L. curvatus,* or *L. salivarius*.

In one embodiment preferably the microorganism is from the genus *Streptococcus*.

In one embodiment preferably the microorganism is from the genus *Enterococcus*.

In one embodiment preferably the microorganism is from the genus *Bifidobacterium*.

Suitably, the microorganism may be a strain from the species *B. lactis. B animalis, B. longum* or *B. bifidum*. Preferably the microorganism may be a strain from the species *B. lactis* such as, for example, *B. lactis* 420 or *B. lactis* HN019.

For some embodiments the microorganism may be a mixture of more than one probiotic microorganisms (preferably more than on probiotic bacteria); a mixture of more than more lactic acid bacteria; or a mixture of one or more probiotic microorganisms (preferably probiotic bacteria) and one or more lactic acid bacteria. Preferably, the mixture may comprise one or more stains from *Lactobacillus* spp, and/or *Bifidobacterium* spp.

In one embodiment preferably the microorganism is at least one strain of *Lactobacillus* spp.

In one embodiment preferably the microorganism is at least one strain of *Lactobacillus acidophilus*.

In one embodiment preferably the microorganism is at least one strain of *Lactobacillus curvatus*.

In one embodiment preferably the microorganism is at least one strain of *Lactobacillus salivarius*.

The microorganism, preferably a *Lactobacillus* spp. such as *L. acidophilus, L. salivarius* and *L. curvatus* for example, for use in accordance with the present invention is preferably a gram-positive strain. Advantageously it may be a catalase-negative strain, with a homofermentative metabolism giving rise to the production of lactic acid.

The microorganism, preferably a *Lactobacillus* spp. such as *L. acidophilus, L. salivarius* and *L. curvatus* for example, for use in accordance with the present invention may also produce a bacteriocin, such as for example lactacin, active against other microorganisms.

Preferably, the microorganism, preferably a *Lactobacillus* spp. such as *L. acidophilus, L. salivarius* and *L. curvatus* for example, for use in accordance with the present invention has a good resistance to pepsin, under acid pH conditions, a good resistance to pancreatin and/or a good tolerance to the bile salts.

In one embodiment, the microorganism, preferably a *Lactobacillus* spp. such as *L. acidophilus* for example, according to the present invention may be a microorganism, preferably a *Lactobacillus* spp. such as *L. acidophilus* for example, which may be described as "hydrophobic", i.e. one having a strong affinity to polar or non-polar hydrophobic organic solvents, such as for example n-decane, chloroform, hexadecane or xylene.

The *Lactobacillus acidophilus* preferred according to the present invention may be The Lactobacillus acidophilus preferred according to the present invention may be Lactobacillus acidophilus PTA-4797. This strain of Lactobacillus acidophilus has been registered by Rhodia Chimie, 26, quai Alphonse Le Gallo, 92 512 BOULOGNE-BILLANCOURT Cedex France, currently located at American Type Culture Collection, 10801 University Blvd., Manassas Va. 20110-2209 USA in accordance with the Budapest Treaty at the American Type Culture Collection (ATCC), on Nov. 15, 2002, where it is recorded under registration number PTA-4797. The strains will be made available if a patent office signatory to the Budapest Treaty certifies that one's rights to receive, or if a U.S. Patent is issued citing the strains, and ATCC is instructed by the United States Patent & Trademark Office or the depositor to release said strains.

The strain of *Lactobacillus acidophilus* for use in accordance with the present invention may be in the form of a mixture with other lactic acid bacteria. The lactic acid bacteria likely to be suitable according to the invention include any lactic acid bacteria usually employed in the agricultural, food or pharmaceutical industries.

Advantageously, where the product is a foodstuff, the viable micro-organism and/or soluble metabolites produced by said micro-organism should remain effective through the normal "sell-by" or "expiration" date during which the food product is offered for sale by the retailer. Preferably, the effective time should extend past such dates until the end of the normal freshness period when food spoilage becomes apparent. The desired lengths of time and normal shelf life will vary from foodstuff to foodstuff and those of ordinary skill in the art will recognise that shelf-life times will vary upon the type of foodstuff; the size of the foodstuff, storage temperatures, processing conditions, packaging material and packaging equipment.

In one embodiment preferably the microorganism is not *Helicobacter pylori*.

Caco-2 Cell-Based Exposure Assay

The human colorectal carcinoma cell line Caco-2 is maintained at 37° C. and 5% $CO_2$ in Dulbecco's MEM (Biochrom AG) supplemented with 20% fetal bovine serum (FBS, Gibco) 2 mM stable glutamine (Biochrom AG) and 1× non-essential amino acids (Biochrom AG)) 20 $Uml^{-1}$ penicillin (Gibco), 20 $\mu gml^{-1}$ streptomycin (Gibco) and 0.5 $\mu gml^{-1}$ amphotericin (Gibco). When subcultured the cells are washed with 1×PBS (Gibco) and detached with Tryple Select (Gibco).

To determine the effects of various microorganisms and/or metabolite thereof on the gut hormone, such as PYY, $6.6 \times 10^5/cm^2$ Caco-2 cells are seeded and differentiated in collagen-coated Transwell cell culture inserts (Corning) according to a 5 day protocol (Yamashita et al. 2001, J. Pharm. Sci. 91(3): 669-679). After seeding into Transwell inserts the Caco-2 cells are maintained for 48 h in medium consisting of Dulbecco's MEM (Biochrom AG), 10% fetal bovine serum (FBS, Gibco), 2 mM stable glutamine (Biochrom AG), and 1× non-essential amino acids but no antibiotics. After 48 h the medium is changed with Enterostim medium (BD Biosciences) supplemented with MITO+ serum extender (BD Biosciences) added to the medium according to protocol provided by the manufacturer. The cells are used in experiments at fourth day after seeding into Transwell inserts or after the transpithelial electrical resistance has increased into a level indicating cell differentiation. Neither antibiotics nor serum are used in all the experiments. The metabolites and/or various microorganisms are added on the apical side of the insert.

After 24 hour exposure, media is discarded, cells inside the inserts are lysed and RNA is extracted using Qiagen's (Germany) RNeasy Mini Kit. DNA is digested using the same manufacturer's RNase free DNase. Reverse transcription is performed using Superscript III reverse transcriptase (Invitrogen) according to the instructions provided by the manufacturer. The hormone (e.g. PYY) expression pattern is determined by real-time quantitative TaqMan PCR (i.e. a relative quantification method—see Holland et al., 1991 Proc. Natl. Acad. Sci. USA August 15; 88(16): 7276-80; and Livak and Scmittgen, 2001 Methods December; 25(4):402-8) using the default settings of an ABI Prism 7000 Sequence Detection instrument (Applied Biosystems)) or by an absolute quantification method such as TaqMan PCR (Applied Biosystems) with ABI Prism 7000 Genetic Analyzer using a oligonucleotide set and a standard oligonucleotide recognizing the hormone (e.g. *homo sapiens* PYY) specifically.

The microbial suspension for use in the above assay may be prepared by culturing the microorganism on a suitable medium. The culture may be centrifuged to form a cell pellet which may be subsequently suspended in a suitable medium, e.g. DMEM.

The metabolite suspension for use in the above assay may be prepared by culturing the microorganism on a suitable culture medium. The culture may be centrifuged and/or the culture broth filtered (suitably sterile-filtered) to provide the metabolite suspension.

Microorganisms which cause a modification in hormone (e.g. an increase in PYY) expression level compared with an untreated control, may be microorganisms according to the present invention and/or which can be used in accordance with the present invention.

A skilled person would readily be able to screen probiotic and non-probiotic microorganisms using the "Caco-2 cell-based exposure assay" to identify specific microorganisms, additional to the ones specifically taught herein, capable of producing the claimed effect.

Combination with Other Components

The microorganism and/or metabolite thereof for use in the present invention may be used in combination with other components. Thus, the present invention also relates to combinations. The microorganism and/or metabolite thereof may be referred to herein as "the composition of the present invention".

The combination of the present invention comprises the composition of the present invention and another component which is suitable for animal or human consumption and is capable of providing a medical or physiological benefit to the consumer.

Other components of the combinations of the present invention include polydextrose, such as Litesse®, and/or a maltodextrin and/or lactitol. These other components may be optionally added to the composition to assist the drying process and help the survival of the microorganisms.

Further examples of other suitable components include one or more of: thickeners, gelling agents, emulsifiers, binders, crystal modifiers, sweeteners (including artificial sweeteners), rheology modifiers, stabilisers, anti-oxidants, dyes, enzymes, carriers, vehicles, excipients, diluents, lubricating agents, flavouring agents, colouring matter, suspending agents, disintegrants, granulation binders etc. These other components may be natural. These other components may be prepared by use of chemical and/or enzymatic techniques.

In one embodiment the microorganism and/or metabolite thereof may be encapsulated.

In one preferred embodiment the microorganism and/or metabolite thereof for use in the present invention may be used in combination with one or more lipids.

For example, the microorganism and/or metabolite thereof for use in the present invention may be used in combination with one or more lipid micelles. The lipid micelle may be a simple lipid micelle or a complex lipid micelle.

The lipid micelle may be an aggregate of orientated molecules of amphipathic substances.

The lipid micelles may be an aggregate, of colloidal dimensions, of orientated molecules of amphipathic substances existing in equilibrium in solution with the chemical species from which it is formed. Micelles are generally electrically charged. In aqueous solution the individual molecules of the micellar aggregate are oriented with their polar groups pointing towards the aqueous medium and their hydrophobic moiety directed into the centre of the micelle.

The lipid micelles may comprise a lipid and/or an oil.

Therefore in one embodiment the present invention provides the use of a combination of at least one strain of a microorganism and/or a metabolite thereof and a lipid micelle for modulating satiety signalling and/or for treating and/or preventing excess weight (or obesity) and/or a disease caused by excess weight (or obesity).

As used herein the term "thickener or gelling agent" refers to a product that prevents separation by slowing or preventing the movement of particles, either droplets of immiscible liquids, air or insoluble solids. Thickening occurs when individual hydrated molecules cause an increase in viscosity, slowing the separation. Gelation occurs when the hydrated molecules link to form a three-dimensional network that traps the particles, thereby immobilising them.

The term "stabiliser" as used here is defined as an ingredient or combination of ingredients that keeps a product (e.g. a food product) from changing over time.

The term "emulsifier" as used herein refers to an ingredient (e.g. a food product ingredient) that prevents the separation of emulsions. Emulsions are two immiscible substances, one present in droplet form, contained within the other. Emulsions can consist of oil-in-water, where the droplet or dispersed phase is oil and the continuous phase is water; or water-in-oil, where the water becomes the dispersed phase and the continuous phase is oil. Foams, which are gas-in-liquid, and suspensions, which are solid-in-liquid, can also be stabilised through the use of emulsifiers. Aeration can occur in a three-phase system where air is entrapped by liquid oil then stabilised by agglomerated fat crystals stabilised with an emulsifier. Emulsifiers have a polar group with an affinity for water (hydrophilic) and a non-polar group which is attracted to oil (lipophilic). They are absorbed at the interfaces of the two substances, providing an interfacial film acting to stabilise the emulsion. The hydrophilic/lipophilic properties of emulsifiers are affected by the structure of the molecule. These properties are identified by the hydrophilic/lipophilic balance (HLB) value. Low HLB values indicate greater lipophilic tendencies which are used to stabilise water-in-oil emulsions. High HLB values are assigned to hydrophilic emulsifiers, typically used in oil-in-water emulsions. These values are derived from simple systems. Because foods often contain other ingredients that affect the emulsification properties, the HLB values may not always be a reliable guide for emulsifier selection.

As used herein the term "binder" refers to an ingredient (e.g. a food ingredient) that binds the product together through a physical or chemical reaction. During "gelation" for instance, water is absorbed, providing a binding effect. However, binders can absorb other liquids, such as oils, holding them within the product. In the context of the present invention binders would typically be used in solid or low-moisture products for instance baking products: pastries, doughnuts, bread and others.

The term "crystal modifier" as used herein refers to an ingredient (e.g. a food ingredient) that affects the crystallisation of either fat or water. Stabilisation of ice crystals is important for two reasons. The first is directly related to the product stability from a separation standpoint. The more freeze/thaw cycles a product encounters, the larger the ice crystals become. These large crystals can break down product structure, either naturally occurring, as in the case of cell walls, or that which is created by "elation". Because the water is no longer held in place, the product may exhibit syneresis, or weeping, after thawing. Secondly, in the case of a product which is consumed frozen, these large crystals result in an undesirable, gritty mouth feel.

"Carriers" or "vehicles" mean materials suitable for compound administration and include any such material known in the art such as, for example, any liquid, gel, solvent, liquid diluent, solubilizer, or the like, which is non-toxic and which does not interact with any components of the composition in a deleterious manner.

Examples of nutritionally acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

Examples of excipients include one or more of: microcrystalline cellulose and other celluloses, lactose, sodium citrate, calcium carbonate, dibasic calcium phosphate, glycine, starch, milk sugar and high molecular weight polyethylene glycols.

Examples of disintegrants include one or more of: starch (preferably corn, potato or tapioca starch), sodium starch glycollate, croscarmellose sodium and certain complex silicates.

Examples of granulation binders include one or more of: polyvinylpyrrolidone, hydroxypropylmethylcellulose (HPMC), hydroxypropylcellulose (HPC), sucrose, maltose, gelatin and acacia.

Examples of lubricating agents include one or more of: magnesium stearate, stearic acid, glyceryl behenate and talc.

Examples of diluents include one or more of: water, ethanol, propylene glycol and glycerin, and combinations thereof.

The other components may be used simultaneously (e.g. when they are in admixture together or even when they are delivered by different routes) or sequentially (e.g. they may be delivered by different routes).

Preferably, when the composition of the present invention when admixed with any other components, the microorganisms remain viable.

As used herein the term "component suitable for animal or human consumption" means a compound which is or can be added to the composition of the present invention as a supplement which may be of nutritional benefit, a fibre substitute or have a generally beneficial effect to the consumer. The ingredients can be used in a wide variety of products that require gelling, texturising, stabilising, suspending, film-forming and structuring, retention of juiciness, without adding unnecessary viscosity. Preferably, the ingredients will be able to improve the shelf life and stability of the viable culture.

The components may be prebiotics such as alginate, xanthan, pectin, locust bean gum (LBG), inulin, guar gum, galacto-oligosaccharide (GOS), fructo-oligosaccharide (FOS), polydextrose (i.e. Litesse®), lactitol, lactosucrose, soybean oligosaccharides, palatinose, isomalto-oligosaccharides, gluco-oligosaccharides and xylo-oligosaccharides.

The optimum amount of the composition to be used in the combination of the present invention will depend on the product to be treated and/or the method of contacting the product with the composition and/or the intended use for the same. The amount of viable microorganism used in the compositions should be a sufficient amount to be effective and to remain sufficiently effective in improving the aroma, flavour, mildness, consistency, texture, body, mouth feel, viscosity, structure and/or organoleptic properties, nutrition and/or health benefits of food products containing said composition. This length of time for effectiveness should extend up to at least the time of utilisation of the product.

Concentrates

The compositions for use in the present invention may be in the form of concentrates. Typically these concentrates comprise a substantially high concentration of a viable microorganism and/or a metabolite thereof. The microorganism and/or metabolite thereof may be referred to herein as "the composition of the present invention" or "compositions".

Powders, granules and liquid compositions in the form of concentrates may be diluted with water or resuspended in water or other suitable diluents, for example, an appropriate growth medium such as milk or mineral or vegetable oils, to give compositions ready for use.

The combinations of the present invention in the form of concentrates may be prepared according to methods known in the art.

In one aspect of the present invention the product is contacted by a composition in a concentrated form. Preferably, the product is contacted by a spray-dried and/or resuspended composition.

The compositions of the present invention may be spray-dried or freeze-dried by methods known in the art.

Typical processes for making particles using a spray drying process involve a solid material which is dissolved in an appropriate solvent (e.g. a culture of a micro-organism in a fermentation medium). Alternatively, the material can be suspended or emulsified in a non-solvent to form a suspension or emulsion. Other ingredients (as discussed above) or components such as anti-microbial agents, stabilising agents, dyes and agents assisting with the drying process may optionally be added at this stage.

The solution then is atomised to form a fine mist of droplets. The droplets immediately enter a drying chamber where they contact a drying gas. The solvent is evaporated from the droplets into the drying gas to solidify the droplets, thereby forming particles. The particles are then separated from the drying gas and collected.

Products

Any product which can benefit from the composition may be used in the present invention. These include but are not limited to fruit conserves and dairy foods and dairy food-derived products, cosmetic and pharmaceutical products. The microorganism and/or metabolite thereof may be referred to herein as "the composition of the present invention" or "the composition".

By way of example, the composition of the present invention can be used as an ingredient to soft drinks, a fruit juice or a beverage comprising whey protein, health teas, cocoa drinks, milk drinks and lactic acid bacteria drinks, yoghurt and drinking yoghurt, cheese, ice cream, water ices and desserts, confectionery, biscuits cakes and cake mixes, snack foods, balanced foods and drinks, fruit fillings, care glaze, chocolate bakery filling, cheese cake flavoured filling, fruit flavoured cake filling, cake and doughnut icing, instant bakery filling creams, fillings for cookies, ready-to-use bakery filling, reduced calorie filling, adult nutritional beverage, acidified soy/juice beverage, aseptic/retorted chocolate drink, bar mixes, beverage powders, calcium fortified soy/plain and chocolate milk, calcium fortified coffee beverage.

The composition can further be used as an ingredient in food products such as American cheese sauce, anti-caking agent for grated & shredded cheese, chip dip, cream cheese, dry blended whip topping fat free sour cream, freeze/thaw dairy whipping cream, freeze/thaw stable whipped tipping, low fat and light natural cheddar cheese, low fat Swiss style yoghurt, aerated frozen desserts, hard pack ice cream, label friendly, improved economics & indulgence of hard pack ice cream, low fat ice cream: soft serve, barbecue sauce, cheese dip sauce, cottage cheese dressing, dry mix Alfredo sauce, mix cheese sauce, dry mix tomato sauce and others.

For certain aspects, preferably the present invention may be used in connection with yoghurt production, such as fermented yoghurt drink, yoghurt, drinking yoghurt, cheese, fermented cream, milk based desserts and others.

Suitably, the composition can be further used as an ingredient in one or more of cheese applications, meat applications, or applications comprising protective cultures.

The present invention also provides a method of preparing a food or a food ingredient, the method comprising admixing the composition according to the present invention with another food ingredient.

Advantageously, the present invention relates to products that have been contacted with the composition of the present invention (and optionally with other components/ingredients), wherein the composition is used in an amount to be capable of improving the nutrition and/or health benefits of the product.

As used herein the term "contacted" refers to the indirect or direct application of the composition of the present invention to the product. Examples of the application methods which may be used, include, but are not limited to, treating the product in a material comprising the composition, direct application by mixing the composition with the product, spraying the composition onto the product surface or dipping the product into a preparation of the composition.

Where the product of the invention is a foodstuff; the composition of the present invention is preferably admixed with the product. Alternatively, the composition may be included in the emulsion or raw ingredients of a foodstuff. In a further alternative, the composition may be applied as a seasoning, glaze, colorant mixture, and the like.

For some applications, it is important that the composition is made available on or to the surface of a product to be affected/treated. This allows the composition to impart one or more of the following favourable characteristics: nutrition and/or health benefits.

The compositions of the present invention may be applied to intersperse, coat and/or impregnate a product with a controlled amount of a viable microorganism.

Food

The composition of the present invention may be used as—or in the preparation of—a food. Here, the term "food" is used in a broad sense—and covers food for humans as well as food for animals (i.e. a feed). In a preferred aspect, the food is for human consumption.

The food may be in the form of a solution or as a solid—depending on the use and/or the mode of application and/or the mode of administration.

When used as—or in the preparation of—a food—such as functional food—the composition of the present invention may be used in conjunction with one or more of: a nutritionally acceptable carrier, a nutritionally acceptable diluent, a nutritionally acceptable excipient, a nutritionally acceptable adjuvant, a nutritionally active ingredient.

Preferably, the composition is used to ferment milk or sucrose fortified milk or lactic media with sucrose and/or maltose where the resulting media containing all components of the composition—i.e. said microorganism according to the present invention—can be added as an ingredient to yoghurt milk in suitable concentrations—such as for example in concentrations in the final product which offer a daily dose of $10^6$-$10^{10}$ cfu. The microorganism according to the present invention may be used before or after fermentation of the yoghurt.

For some aspects the microorganisms according to the present invention are used as—or in the preparation of—animal feeds, such as livestock feeds, in particular poultry (such as chicken) feed, or pet food.

Food Ingredient

The composition of the present invention may be used as a food ingredient and/or feed ingredient.

As used herein the term "food ingredient" or "feed ingredient" includes a formulation which is or can be added to functional foods or foodstuffs as a nutritional supplement.

The food ingredient may be in the form of a solution or as a solid—depending on the use and/or the mode of application and/or the mode of administration.

Food Supplements

The composition of the present invention may be—or may be added to—food supplements.

Functional Foods

The composition of the present invention may be—or may be added to—functional foods.

As used herein, the term "functional food" means food which is capable of providing not only a nutritional effect, but is also capable of delivering a further beneficial effect to consumer.

Accordingly, functional foods are ordinary foods that have components or ingredients (such as those described herein) incorporated into them that impart to the food a specific functional—e.g. medical or physiological benefit—other than a purely nutritional effect.

Although there is no legal definition of a functional food, most of the parties with an interest in this area agree that they are foods marketed as having specific health effects beyond basic nutritional effects.

Some functional foods are nutraceuticals. Here, the term "nutraceutical" means a food which is capable of providing not only a nutritional effect and/or a taste satisfaction, but is also capable of delivering a therapeutic (or other beneficial) effect to the consumer. Nutraceuticals cross the traditional dividing lines between foods and medicine.

Surveys have suggested that consumers place the most emphasis on functional food claims relating to heart disease. Preventing cancer is another aspect of nutrition which interests consumers a great deal, but interestingly this is the area that consumers feel they can exert least control over. In fact, according to the World Health Organization, at least 35% of cancer cases are diet-related. Furthermore claims relating to osteoporosis, gut health and obesity effects are also key factors that are likely to incite functional food purchase and drive market development.

Probiotic

For some applications, it is believed that the viable lactic acid microorganisms in the composition of the present invention can exert a probiotic culture effect. It is also within the scope of the present invention to add to the composition of the present invention further probiotic and/or prebiotics.

Here, a prebiotic is:

"a non-digestible food ingredient that beneficially affects the host by selectively stimulating the growth and/or the activity of one or a limited number of beneficial bacteria".

The term "probiotic culture" as used herein defines live microorganisms (including bacteria or yeasts for example) which, when for example ingested or locally applied in sufficient numbers, beneficially affects the host organism, i.e. by conferring one or more demonstrable health benefits on the host organism. Probiotics may improve the microbial balance in one or more mucosal surfaces. For example, the mucosal surface may be the intestine, the urinary tract, the respiratory tract or the skin. The term "probiotic" as used herein also encompasses live microorganisms that can stimulate the beneficial branches of the immune system and at the same time decrease the inflammatory reactions in a mucosal surface, for example the gut.

Whilst there are no lower or upper limits for probiotic intake, it has been suggested that at least $10^6$-$10^{12}$, preferably at least $10^6$-$10^{10}$, preferably $10^8$-$10^9$, cfu as a daily dose will be effective to achieve the beneficial health effects in a host organism, such as a human.

In addition to the probiotic effect the microorganism according to the present invention may have, it is also within the scope of the present invention to provide prebiotics as other compounds which can be included in a combination along with the composition. The microorganism according to the present invention and/or a metabolite thereof may be herein referred to as "the composition". The prebiotic component of the combination comprising the composition of the present invention are characterised with slow fermentation in the large bowel. Such prebiotics can exert a positive effect on the gut flora, specifically in the left side of the colon, an area of the gut which is especially prone to disorders in particular bowel cancer and ulcerative colitis.

Prebiotics are typically non-digestible carbohydrate (oligo- or polysaccharides) or a sugar alcohol which is not degraded or absorbed in the upper digestive tract. Known prebiotics used in commercial products and useful in accordance with the present invention include inulin (fructo-oligosaccharide, or FOS) and transgalacto-oligosaccharides (GOS or TOS). Other suitable, prebiotics include palatinoseoligosaccharide, soybean oligosaccharide, gentiooligosaccharide, xylooligomers, non-degradable starch, lactosaccharose, lactulose, lactitol, maltitol, polydextrose (i.e. Litesse®) or the like.

In one embodiment the present invention relates to the combination of a microorganism and/or metabolite thereof according to the present invention with a prebiotic.

The prebiotic for use in this combination may be one or more of the following: inulin (fructo-oligosaccharide, or FOS) and transgalacto-oligosaccharides (GOS or TOS). Other suitable, prebiotics include palatinoseoligosaccharide, soybean oligosaccharide, gentiooligosaccharide, xylooligomers, non-degradable starch, lactosaccharose, lactulose, lactitol, maltitol, polydextrose (i.e. Litesse®), or lactitol.

The prebiotic may be administered simultaneously with (e.g. in admixture together with or delivered simultaneously by the same or different routes) or sequentially to (e.g. by the same or different routes) the microorganism according to the present invention and/or a metabolite thereof.

The present invention contemplates the use of a microorganism and/and/or a metabolite thereof in combination with a prebiotic in the manufacture of a medicament for use in inducing satiety and/or treating or preventing excess weight or obesity.

Synbiotics

The present invention also contemplates using both pre- and probiotics as ingredients in a combination along with the composition of the present invention which when combined, become synbiotics. The microorganism according the present invention and/or a metabolite thereof may be referred to herein as "the composition". The purpose of this is to combine the effects of new beneficial bacteria and the stimulation of the body-own beneficial bacteria. There is a high potential in the development and the consumption of such mixtures, since some of these may well show powerful synergistic nutritional and/or health effects.

Thus the composition of the present invention may be specifically designed to contain different components which can provide a synbiotic effect to the consumer.

Pharmaceutical

The composition of the present invention may be used as—or in the preparation of—a pharmaceutical. Here, the term "pharmaceutical" is used in a broad sense—and covers pharmaceuticals for humans as well as pharmaceuticals for animals (i.e. veterinary applications). In a preferred aspect, the pharmaceutical is for human use and/or for animal husbandry.

The pharmaceutical can be for therapeutic purposes—which may be curative or palliative or preventative in nature. The pharmaceutical may even be for diagnostic purposes.

When used as—or in the preparation of—a pharmaceutical, the composition of the present invention may be used in conjunction with one or more of: a pharmaceutically acceptable carrier, a pharmaceutically acceptable diluent, a pharmaceutically acceptable excipient, a pharmaceutically acceptable adjuvant, a pharmaceutically active ingredient.

The pharmaceutical may be in the form of a solution or as a solid—depending on the use and/or the mode of application and/or the mode of administration.

Pharmaceutical Ingredient

The microorganisms of the present invention may be used as pharmaceutical ingredients. Here, the composition may be the sole active component or it may be at least one of a number (i.e. 2 or more) of active components.

The pharmaceutical ingredient may be in the form of a solution or as a solid—depending on the use and/or the mode of application and/or the mode of administration.

Forms

The microorganism of the present invention and/or a metabolite thereof may be used in any suitable form—whether when alone or when present in a combination with other components or ingredients. The microorganism of the present invention and/or a metabolite thereof may be referred to herein as "the composition". Likewise, combinations comprising the composition of the present invention and other components and/or ingredients (i.e. ingredients—such as food ingredients, functional food ingredients or pharmaceutical ingredients) may be used in any suitable form.

The microorganism of the present invention may be used in the form of solid or liquid preparations or alternatives thereof. Examples of solid preparations include, but are not limited to, tablets, capsules, dusts, granules and powders which may be wettable, spray-dried or freeze-dried. Examples of liquid preparations include, but are not limited to, aqueous, organic or aqueous-organic solutions, suspensions and emulsions.

Suitable examples of forms include one or more of: tablets, pills, capsules, ovules, solutions or suspensions, which may contain flavouring or colouring agents, for immediate-, delayed-, modified-, sustained-, pulsed- or controlled-release applications.

By way of example, if the composition of the present invention is used in a tablet form—such for use as a functional ingredient—the tablets may also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc may be included.

Examples of nutritionally acceptable carriers for use in preparing the forms include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

Preferred excipients for the forms include lactose, starch, a cellulose, milk sugar or high molecular weight polyethylene glycols.

For aqueous suspensions and/or elixirs, the composition of the present invention may be combined with various sweetening or flavouring agents, colouring matter or dyes, with emulsifying and/or suspending agents and with diluents such as water, propylene glycol and glycerin, and combinations thereof.

The forms may also include gelatin capsules; fibre capsules, fibre tablets etc.; or even fibre beverages.

Further examples of form is in the form of a cream for example. For some aspects the microorganism and/or a metabolite thereof may be included in pharmaceutical and/or cosmetic creams such as sun creams and/or after-sun creams for example.

In one aspect, the composition according to the present invention may be administered in an aerosol, for example by way of a nasal spray, for instance for administration to the respiratory tract.

EXAMPLES

The present invention will now be described, by way of example only, in which reference may be made to the following figures:

FIG. 1 shows the gene expression pattern of Peptide YY (PYY) in Caco-2 cells treated with *L. acidophilus*. The data was normalized against the RNA amount. The fold difference was calculated as in Livak and Schmittgen, 2001;

EXAMPLE 1

To Analyze the Gene Expression Pattern of Peptide YY (PYY) in Caco-2 Treated with *L. acidophilus*.

Method:

The human colonic carcinoma cell line Caco-2 were cultivated on semiporous cell culture inserts and differentiated according to a 5-day differentiation protocol using differentiation media (DM) composed of Entero-STIM medium supplemented with MITO+ serum extender and containing no antibiotics. The differentiation was monitored using TER-measurements and alkaline phosphatase activity measurement.

The *Lactobacillus acidophilus* (strain PTA-4797) bacteria were cultivated on MRS broth supplemented with 1% (weight/vol) glucose until the $OD_{600}$ reached 0.6-0.7. The *L. acidophilus* treatment was added into apical side of the cell culture insert and incubated for 24 hours. The RNA was isolated from the cells according to the protocol provided by RNeasy mini kit (Qiagen), and the cDNA synthesized using Superscript III reverse transcriptase (Invitrogen). The gene expression pattern was monitored either using the SYBR Green (Applied Biosystems) with ABI Prism 7000 Genetic Analyzer with primers specific for homo sapiens peptide YY. Th forward primer was: 5' GGA GGC CTC AGC TTG ACC 3' (SEQ ID NO: 1) and reverse primer: 5'TGC GCA CGA ACA CCA TAG 3' (SEQ ID NO: 2). The obtained threshold cycle (Ct), which is the PCR-cycle at which the fluorescence intensity crosses a background threshold value, was transformed into relative expression value using the method of Livak et al. (2001).

As a control, Caco-2 cells grown similarly on cell culture inserts without treatment with *L. acidophilus*.

Results:

The results from alkaline phosphatase activity as well as TER measurements indicate that the cells were well differentiated (data not shown).

Figure 1:
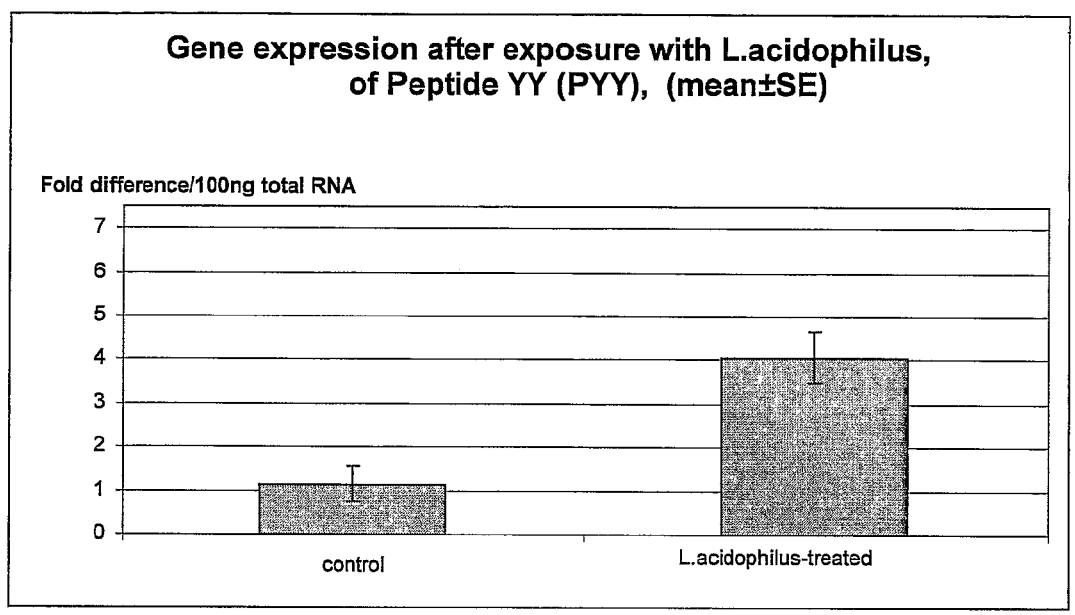

The gene expression analysis shows that the expression of satiety marker peptide YY (PYY). The peptide YY (PYY) expression increased with 255% when compared to control when the CaCo-2 cells were treated with *L. acidophilus* ($p<0.05$, ANOVA) (FIG. 1).

The *L. acidophilus*—treatment of Caco-2 cells increased the expression of a satiety marker, peptide YY. The result indicates that consumption of *Lactobacillus acidophilus* can increase postprandial satiety by increasing satiety signalling in the intestine.

EXAMPLE 2

In vitro Experiment Mimicking the Meal with Glucose Experiment with Differentiated Caco-2 Cells. Effect of *L. acidophilus* Conditioned Culture Broth in Cells Treated with Various Amounts of Glucose The Caco-2 were cultivated on semiporous cell culture inserts and differentiated according to a 5-day differentiation protocol using differentiation media (DM) composed of Entero-STIM medium supplemented with MITO+ serum extender and containing no antibiotics. The differentiation was monitored using TER-measurements and alkaline phosphatase activity measurement. On the fourth day of the experiment, the medium was changed with a medium containing no glucose on both sides of the insert and the cells were starved from glucose for 24 h.

The treatments of the Caco2-cells consisted of control cells, which were treated on the apical side with 0.5 mM, and 5 mM glucose containing medium, and test cells, which were treated on the apical side with 0.5 mM and 5 mM glucose containing medium with concomitant addition of *L acidophilus* treatment. In addition, control Caco2-cells without any addition of glucose containing medium on the apical side was included. In all wells 5 mM glucose on the basal side was added. The cells were incubated for 24 h at 37° C., 5% $CO_2$.

The *L. acidophilus* bacteria were cultivated on MRS broth containing no sugar until the $OD_{600}$ reached 0.6-0.7. The cells were centrifuged and the culture broth was sterile-filtered and used in the test mediums.

The RNA was isolated from the Caco2-cells according to the protocol provided by RNeasy mini kit (Qiagen), and the cDNA synthesized using Superscript III reverse transcriptase (Invitrogen). The gene expression pattern of PYY was monitored using the TaqMan probe chemistry (Applied Biosystems) with ABI Prism 7000 Genetic Analyzer using a oligonucleotide set recognizing the *homo sapiens* PYY specifically.

The oligonucleotides included: forward primer: 5' GGA GGC CTC AGC TTG ACC 3' (SEQ ID NO: 1), reverse primer: 5' TGC GCA CGA ACA CCA TAG 3' (SEQ ID NO: 2), and a probe: Universal ProbeLibrary probe #10 (Roche). The obtained threshold cycle (Ct), which is the PCR-cycle at which the fluorescence intensity crosses a background threshold value, was transformed into absolute quantitative value using a standard curve from quantified synthetic oligonucleotides representing the antisense sequence of the target transcript showing inverse log-linear relationship between the copy number and the PCR cycle (Nurmi et al., 2005 Nutrition & Cancer 51 (1): 83-92.) The sequence of this standard oligonucleotide is: 5' TGC GCA CGA ACA CCA TAG CGA TAG CTT GTG AAG CAG ACG AGC AGG AGG TGG AAG GCG AGG GAA GTC CCA AGG GCT GCA CTG CCG CAG GTC AAG CTG AGG CCT CC 3' (SEQ ID NO: 3).

Results

The results from alkaline phosphatase activity as well as TER measurements indicate that the cells were well differentiated (data not shown).

Figure 2:
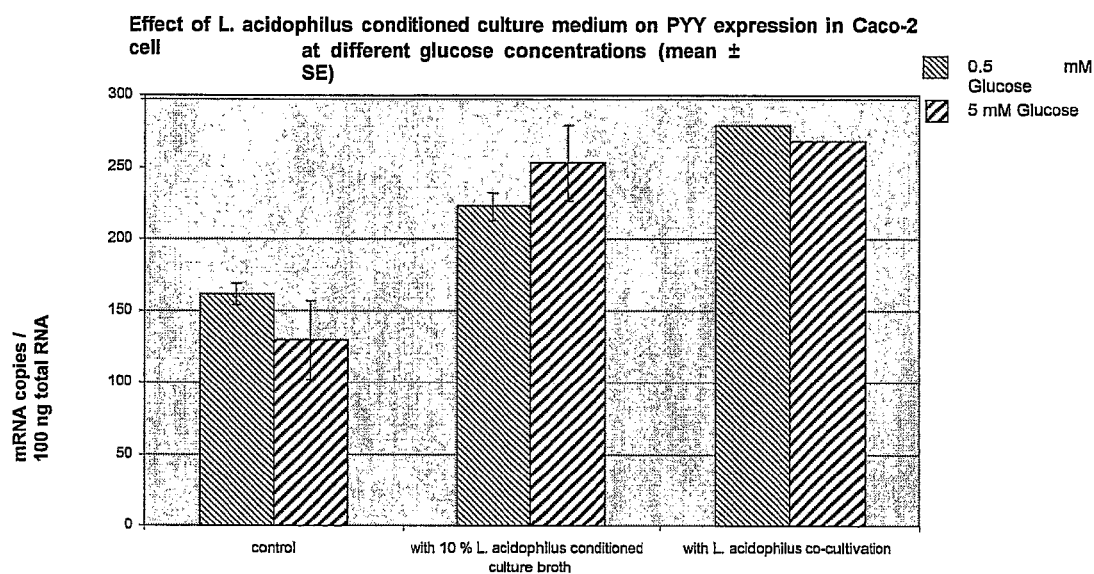
FIG. 2 shows the effect of *L. acidophilus* conditioned culture medium on PYY expression in Caco-2 cells.

The results are shown in FIG. 2.

The addition of *L. acidophilus* culture broth increased the expression of PYY by 1.3-fold in samples containing 0.5 mM glucose (p<0.05, ANOVA) and 2-fold in samples containing 5 mM glucose (p<0.05) compared to the respective control with similar glucose amount). The co-cultivation of *L. acidophilus* together with Caco2 cells increased the expression of PYY by 1.7-fold in samples containing 0.5 mM glucose, and by 2-fold in samples containing 5 mM glucose compared to the respective control cells with similar glucose values.

EXAMPLE 3

In vitro Experiments with Other Probiotics

The Caco-2 were cultivated on semiporous cell culture inserts and differentiated according to a 5-day differentiation protocol using differentiation media (DM) composed of Entero-STIM medium supplemented with MITO+ serum extender and containing no antibiotics. The differentiation was monitored using TER-measurements and alkaline phosphatase activity measurement.

The treatments of the Caco2-cells consisted of control cells, which were treated with Caco-2 culture medium, and test cells, which were treated with probiotic culture broth in Caco-2 culture medium. In addition, control Caco2-cells with addition of MRS broth diluted in Caco-2 culture medium was included. Cells were incubated for 24 hours at 37° C., 5% $CO_2$, The probiotic bacteria were cultivated on MRS broth supplemented with 1% (weight/vol) glucose until the $OD_{600}$ reached 0.6-0.7. The cells were centrifuged and culture broth was sterile-filtered and used in the test medium. The probiotic strains tested included following commercialized strains: *B. lactis* 420 (from Danisco), *B. lactis* HN019 (Trade name Howaru™ Bifido—Danisco A/S) and *L. salivarius* Ls-33 (from Danisco).

The RNA was isolated from the Caco2-cells according to the protocol provided by RNeasy mini kit (Qiagen), and the cDNA synthesized using Superscript III reverse transcriptase (Invitrogen). The gene expression pattern of PYY was monitored using the TaqMan probe chemistry (Applied Biosystems) with ABI Prism 7000 Genetic Analyzer using a oligonucleotide set recognizing the *Homo sapiens* PYY specifically.

The oligonucleotides included: forward primer: 5' GGA GGC CTC AGC TTG ACC 3' (SEQ ID NO: 1), reverse primer: 5'TGC GCA CGA ACA CCA TAG 3' (SEQ ID NO: 2), and a probe: Universal ProbeLibrary probe #10 (Roche). The obtained threshold cycle (Ct), which is the PCR-cycle at which the fluorescence intensity crosses a background threshold value, was transformed into absolute quantitative value using a standard curve from quantified synthetic oligonucleotides representing the antisense sequence of the target transcript showing inverse log-linear relationship between the copy number and the PCR cycle (Nurmi et al., 2005 Nutrition & Cancer 51 (1): 83-92.). The sequence of this standard oligonucleotide is: 5' TGC GCA CGA ACA CCA TAG CGA TAG CTT GTG AAG CAG ACG AGC AGG AGG TGG AAG GCG AGG GAA GTC CCA AGG GCT GCA CTG CCG CAG GTC AAG CTG AGG CCT CC 3' (SEQ ID NO: 3).

Figure 3:
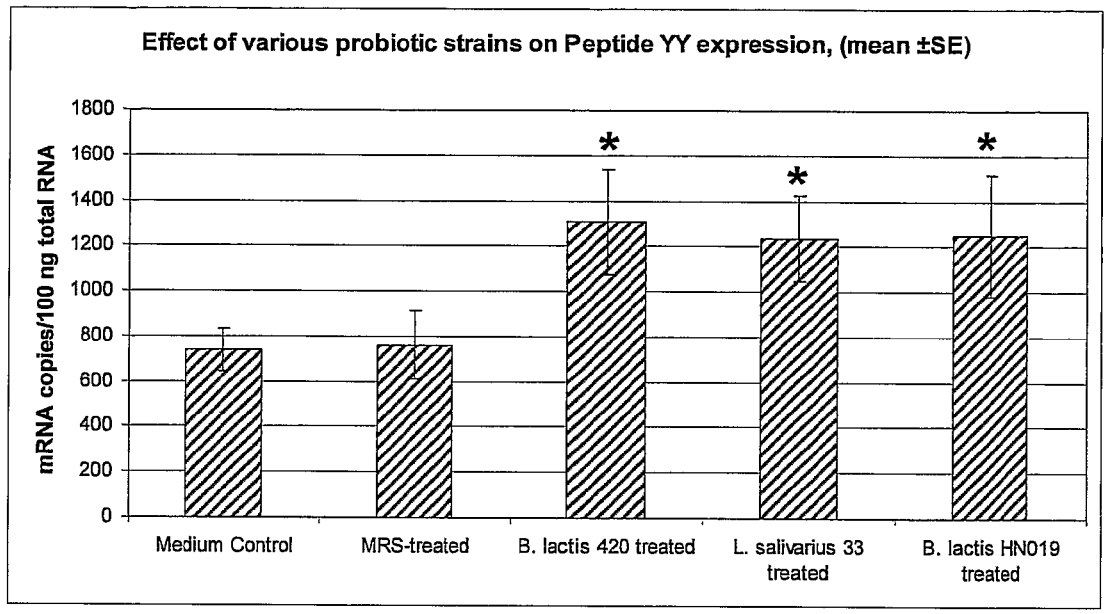
FIG. 3 shows the gene expression of PYY after exposure to different microorganisms having probiotic properties.

Results:

The results are shown in FIG. 3.

The addition of *B. lactis* 420 and *B. Lactis* HN019 increased the expression PYY by 76% and 68%, respectively, compared to the control. The treatment of *L. salivarius* 33 increased the expression of PYY by 67% compared to the control. Therefore, other bacteria than *L. acidophilus* may have the same satiety inducing effect.

EXAMPLE 4

Measure of Satiety Signalling in Blood in Rats:

In this study rat was used as a human model although some physiological differences exist. Unlike in human stomach proximal part of rat stomach is almost free of gastric juice that enables bacteria to survive and ferment the food there. That may cause differences in the satiety between human and rat. Thus the rat plasma obtained using the protocol below will be analysed for neuroendocrinological signals arising from stomach (ghrelin, leptin), intestine (CCK, GLP-1, PYY, orexins) or metabolites in blood circulation (acetic acid, glucose) and their hormonal responses (insulin).

The gastrointestinal tract is rich in endocrine and neuronal cells that synthesize and secrete satiety increasing peptides, cholecystokinin (CCK) and peptide YY (PYY), in the response to the intraluminal stimuli associated with ingestion of a meal. CCK inhibits food intake rapidly, and the duration of inhibition is relatively brief. It is also known that short chain fatty acid produced by gut microbes induce satiety inducing gut hormone PYY. Probiotics may cause also decrease in appetite stimulating peptides ghrelin and orexin. Plasma concentration of those peak before meal and decrease rapidly after that.

Accordingly, attention will be focused on the plasma levels of satiety increasing peptides CCK and PYY and also appetite stimulating peptides ghrelin or orexin as an indicator of the control of short-term food intake after probiotics supplementation. Moreover the plasma concentration of acetic acid will be analysed to see the level of fermentation products in plasma.

Male Wistar rats (HsdRddHan:WIST) weighing 248 g (STDEV 12.1 g) at the start of the experiments were housed at 21° C. in a 12-h light/dark cycle with free access to tap water ad libitum. During the acclimatization period (14 days) the normal cycle was reversed and rats were trained to consume all their food (20 g/day,) within 5 h from the start of the dark cycle at 8 AM. The Formulab Diet 5008 used was a high-energy, high protein diet and it contained Digestible carbohydrates 49.5 5 and fiber. Rats were randomly allocated to two treatment groups of 20 animals each, and one group of 5 rats. The latter group was anesthetized at 8 AM before receiving food to provide fasting blood samples. The remaining groups were: Bifido 420 ($10^{10}$), NCFM ($10^{10}$), NCFM ($10^{10}$)+lactitol (2 g), lactitol (2 g) alone and control group. Lactitol was included as it is known to increase postprandially circulating PYY concentration. All the test items were administered by tube feeding in a volume of 2.5 ml sterile water/animal. Control group was given sterile water without any supplement, in the same conditions. Animals were given standard food after dosing. Each test group was divided into five subgroups and each subgroup was on turn anesthetized for blood sampling at 1, 5, 10 and 24 h after the start of the dark cycle. Rats were anesthetized with carbon dioxide for blood sampling by cardiac puncture.

PYY concentrations will be analysed from plasma according to Gee and Johnson (2005). Other hormones may be analysed including: GLP-1 with radioimmunoassay (RIAs) according to Deacon et al (2002) Am. J. Physiol. Endocrinol. Metab. 282:E873-E879, ghrelin with RIA, CCK according to Paloheimo & Rehfeld (1995), orexin according to Heinonen et al (2005), and acetic acid by HPLC. All blood samples will be taken by cardiac puncture into EDTA tubes. The samples were centrifuged by 1,600×g at 4° C. for 15 minutes. Plasma fraction will be removed and transferred into fresh tubes and stored at −70° C. until analysis.

Trials to Monitor the Food Intake in a Meal:

Male Wistar rats as described above are used. Ten rats are used in each group (control and test diet fed groups of rats).

The rats first have ten days acclimatization to the test, after which the test starts and lasts for ten days. The rats are divided into five groups, one control and four test groups. In all groups the rats are fed ad libitum with control diet. The control group receives saline in gavage once per day and the test groups receive L. acidophilus at amount of $10^8$ and $10^{10}$ in gavage once per day. The rats are preferably fed during dark cycle.

The food intake and the weight gain are monitored after each dark cycle on each rat.

Preliminary investigations suggest that the addition of microorganisms, and particularly probiotic strains, in the food of rats decreases food intake by these rats.

Clinical Trial: Postprandial Satiety Signalling Study on Humans

A pilot study could be conducted with 15-20 volunteers (human subjects). The subjects are their own controls (two separate tests with either control or test drink).

The subjects are preferably an equal number of middle-aged healthy men and women (body mass index BMI approximately 25).

The subjects undergo an overnight-fasting.

Afterwards, they are given test drink (comprising one or more of the strains of interest disclosed in the present specification), and control drink (without the strains of interest).

After, venous blood samples are taken at 0, 2 and 5 hours.

A questionnaire has to be filled by the subjects, to relate the hunger and satiety sensations they had after having had either test or control drink.

In parallel, concentrations of PYY are measured from plasma (Peninsula Laboratories, San Carlos, Calif., USA).

EXAMPLE 5

Experiment with Differentiated Caco-2 Cells. Effect of L. acidophilus Conditioned Culture Broth in Cells Treated with Lipids This experiment is performed to mimic a meal with fatty acids:

The experiment was done with Caco-2 cells which were differentiated according a 5-day protocol (Yamashita, S., Konishi, K., Yamazaki, Y., Taki, Y., Sakane, T., Sezaki, H. & Furuyama, Y. (2002) *J Pharm Sci* 91, 669-79). The cells were differentiated until the transepithelial electrical resistance (TEER) was over 200 ohm×$cm^2$. The complex lipid micelles were prepared according to (Chateau, D., Pauquai, T., Delers, F., Rousset, M., Chambaz, J. & Demignot, S. (2005) *J. Cell Physiol* 202, 767-776) with or without 10% L. acidophilus NCFM metabolites. The Caco-2 cells were treated with the lipid micelles for 3 hours after which the PYY expression was measured from the cells.

Materials & Methods

Caco-2 cells (HTB-37, American Type Culture Collection, ATCC) were maintained at 37° C. in humidified 5% $CO_2$ atmosphere in basal culture medium consisting of Dulbecco's Modified Eagle's Medium (DMEM, Invitrogen Carlsbad, Calif., US) supplemented with 20% FBS (Invitrogen), 2 mM stable glutamine (Invitrogen), 1× non-essential amino acids (Invitrogen), 20 U/ml penicillin (Invitrogen), 20 µg/ml streptomycin (Invitrogen), and 0.5 µg/ml amphotericin (Invitrogen).

The Caco-2 cells were used at passage 26 and plated as 6.6×$10^5$ cells/$cm^2$ on 12-well cell culture inserts (BIOCOAT HTS, BD Biosciences, Le Pont de Claix, France) and differentiated according to a 5-day protocol (Yamashita, S., Konishi, K., Yamazaki, Y., Taki, Y., Sakane, T., Sezaki, H. & Furuyama, Y. (2002) *J Pharm Sci* 91, 669-79). Briefly, after plating, the cells were incubated o/n at 37° C. at humidified 5% $CO_2$ atmosphere in basal cell culture medium without antibiotics after which the medium was aspirated and replaced with differentiation medium (Entero-STIM, BD Biosciences), supplemented with MITO+ serum extender (BD Biosciences) 250 μl/250 ml medium. At 4th day of culture, the medium was replaced, and at $5^{th}$ day the experiment with lipid micelles was conducted.

*L. acidophilus* NCFM (from Danisco Cultures, Paris, France) was cultivated at 37° C. anaerobically in Man, Rogosa and Sharpe (MRS) broth supplemented with 1.0% glucose until the OD600 reached 0.6-0.7. The bacterial cell density was determined with flow cytometry (FACSCalibur, Becton Dickinson, San Jose, Calif., US) as previously described (Apajalahti, J. H., Kettunen, H., Kettunen, A., Holben, W. E., Nurminen, P. H., Rautonen, N. & Mutanen, M. (2002) *Appl. Environ. Microbiol.* 68, 4986-4995). The cell-free supernatants were collected by centrifugation (25° C., 5 min, 3000 g) and supernatant was removed. The *L. acidophilus* NCFM cell-free supernatant (referred later as *L. acidophilus* NCFM metabolites) as well as the MRS control were diluted 10% (v/v) in differentiation medium and complex lipid micelles were prepared into the resulting media (see below).

The complex lipid micelles were prepared into 24 mM taurocholate (Sigma, St Louis, Mo., USA) in differentiation medium. The composition of complex micelles used was: 0.6 mM oleic acid—2 mM taurocholate—0.2 mM 2-mono-oleylglycerol—0.05 mM cholesterol—0.2 mM phosphatidylcholine. One millilitre of micelles was prepared by mixing oleic acid (6 μl of 100 mM stock) with other lipids (2 μl) in a sterile glass tube. The lipids were dried under nitrogen gas at ambient temperature and the residue was dissolved in 83 μl of 24 mM taurocholate in differentiation medium and the volume was brought up to 1 ml either by bare differentiation medium, by differentiation medium consisting of 10% (v/v) MRS, or by differentiation medium consisting of 10% (v/v) *L. acidophilus* NCFM metabolites.

The lipid micelles were applied at fifth day of Caco-2 differentiation on the apical side of the cells, and were left to react with the cells for 3 hours. As controls 10% (v/v) MRS and complex lipid micelles without *L. acidophilus* NCFM metabolites were used. They were prepared into differentiation medium.

After the treatments the cell culture media were aspirated and the cells were lysed with 150 μl of RA1 (Macherey-Nagel, Duren, Germany) supplemented with 1% β-mercaptoethanol (Sigma). The RNA from the cell lysates was collected with Nucleospin 96 RNA isolation kit according to instruction provided by the manufacturer (Macherey-Nagel). The first-strand cDNA synthesis was done with random primers using Superscript III according to the instructions provided by the manufacturer (Invitrogen). The PYY expression pattern in the samples was analyzed using ABI PRISM Sequence Detection System (Applied Biosystems, Foster City, Calif., USA) using oligonucleotides specifically detecting homo sapiens PYY. The oligonucleotides included: forward primer: 5' GGA GGC CTC AGC TTG ACC 3' (SEQ ID NO: 1); reverse primer: 5' TGC GCA CGA ACA CCA TAG 3' (SEQ ID NO: 2); and the probe: Universal ProbeLibrary probe #10 (Roche). The obtained threshold cycle (Ct), which is the PCR-cycle at which the fluorescence intensity crosses a background threshold value, was transformed into absolute quantitative value by using a standard curve from quantified synthetic oligonucleotides representing the antisense sequence of the target transcript showing inverse log-linear relationship between the copy number and the PCR-cycle (Nurmi, J. T., Puolakkainen, P. A. & Rautonen, N. E. (2005) *Nutr Cancer* 51, 83-92). The sequence of this standard oligonucleotide is: 5' TGC GCA CGA ACA CCA TAG CGA TAG CTT GTG AAG CAG ACG AGC AGG AGG TGG AAG GCG AGG GAA GTC CCA AGG GCT GCA CTG CCG CAG GTC AAG CTG AGG CCT CC 3' (SEQ ID NO: 3).

The statistical analysis was done with Student's t-test.

Results

Figure 5:
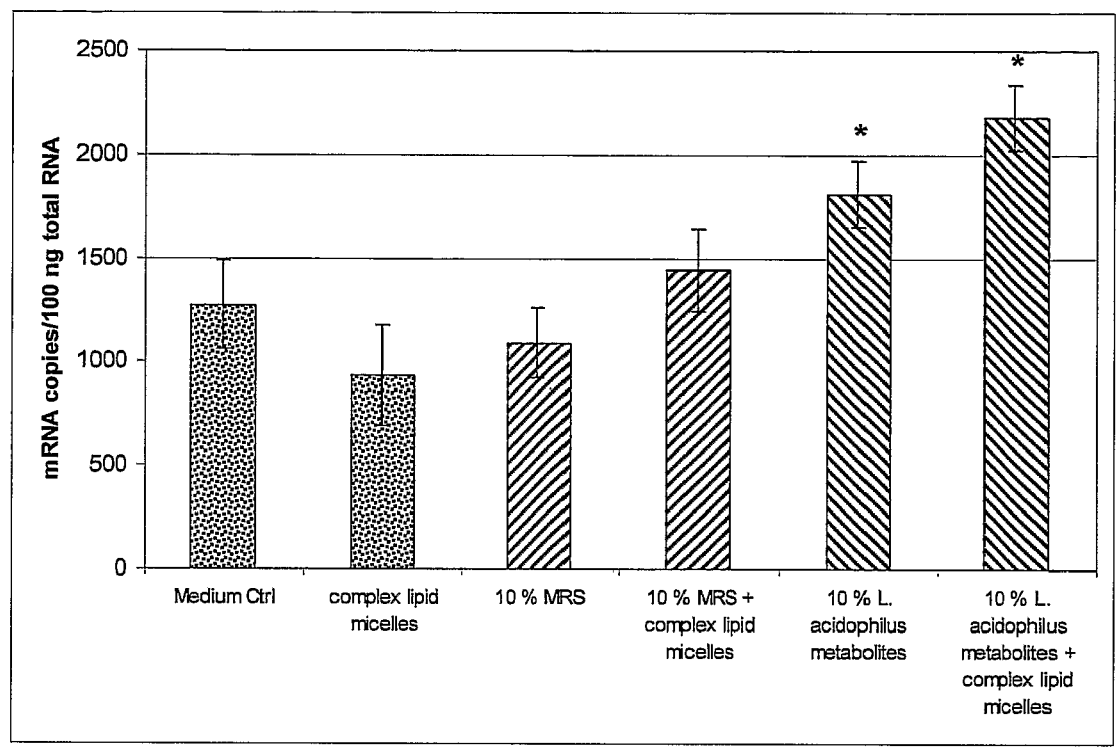
FIG. 5 shows the effects of *L. acidophilus* metabolites; complex lipid micelles and a combination thereof on PYY expression in differentiated caco-2 cells.

The results are shown in FIG. 5.

The expression of satiety marker peptide YY (PYY) increased when Caco-2 cells were treated either with *L. acidophilus* NCFM metabolites alone or combined with the complex lipid micelles.

In the experiment with complex lipid micelles (composed of 0.6 mM oleic acid, 2 mM 2-mono-oleylglycerol, 0.2 mM cholesterol and 0.05 mM L-α-phosphatidylcholine), the MRS broth combined with the complex lipid micelle mixture did not induce the PYY expression when compared with the treatment with complex lipid micelles alone. The *L. acidophilus* NCFM metabolites increased the expression of PYY compared to the controls (p<0.05 when compared to complex lipid micelles alone, and p=0.05 when compared to 10% MRS alone). When the complex lipid micelles were combined with the 10% *L. acidophilus* NCFM metabolites it further increased the PYY expression (p<0.05 when compared either to complex lipid micelle treatment, or to 10% MRS treatment).

EXAMPLE 6

Effect of *L. acidophilus* NCFM Bacterial Cells on Differentiated Caco-2 Cells Treated with Lipids The experiment was done with Caco-2 cells which were differentiated according a 5-day protocol (Yamashita, S., Konishi, K., Yamazaki, Y., Taki, Y., Sakane, T., Sezaki, H. & Furuyama, Y. (2002) *J Pharm Sci* 91, 669-79). The cells were differentiated until the transepithelial electrical resistance (TEER) was over 200 ohm×$cm^2$. The complex lipid micelles were prepared according to (Chateau, D., Pauquai, T., Delers, F., Rousset, M., Chambaz, J. & Demignot, S. (2005) *J. Cell Physiol* 202, 767-776), with or without *L. acidophilus* NCFM bacterial cells in a ratio of 50 bacterial cells to one Caco-2 cell. The Caco-2 cells were treated with the lipid micelles for 3 hours after which the PYY expression was measured from the cells.

Materials & Methods

Caco-2 cells (HTB-37, American Type Culture Collection, ATCC) were maintained at 37° C. in humidified 5% $CO_2$ atmosphere in basal culture medium consisting of Dulbecco's Modified Eagle's Medium (DMEM, Invitrogen Carlsbad, Calif., US) supplemented with 20% FBS (Invitrogen), 2 mM stable glutamine (Invitrogen), 1× non-essential amino acids (Invitrogen), 20 U/ml penicillin (Invitrogen), 20 μg/ml streptomycin (Invitrogen), and 0.5 μg/ml amphotericin (Invitrogen).

The Caco-2 cells were used at passage 26 and plated as 6.6×$10^5$ cells/$cm^2$ on 12-well cell culture inserts (BIOCOAT HTS, BD Biosciences, Le Pont de Claix, France) and differentiated according to a 5-day protocol (Yamashita, S., Konishi, K., Yamazaki, Y., Taki, Y., Sakane, T., Sezaki, H. & Furuyama, Y. (2002) *J Pharm Sci* 91, 669-79). Briefly, after plating, the cells were incubated o/n at 37° C. at humidified 5% $CO_2$ atmosphere in basal cell culture medium without antibiotics after which the medium was aspirated and replaced with differentiation medium (Entero-STIM, BD Biosciences), supplemented with MITO+ serum extender (BD Biosciences) 250 µl/250 ml medium. At 4th day of culture, the medium was replaced, and at $5^{th}$ day the experiment with lipid micelles was conducted.

*L. acidophilus* NCFM (from Danisco Cultures, Paris, France) was cultivated at 37° C. anaerobically in Man, Rogosa and Sharpe (MRS) broth supplemented with 1.0% (weight/volume) glucose until the OD600 reached 0.6-0.7. The bacterial cell density was determined with flow cytometry (FACSCalibur, Becton Dickinson, San Jose, Calif., US) as previously described (Apajalahti, J. H., Kettunen, H., Kettunen, A., Holben, W. E., Nurminen, P. H., Rautonen, N. & Mutanen, M. (2002) *Appl. Environ. Microbiol.* 68, 4986-4995). The bacterial cells were collected by centrifugation (25° C., 5 min, 3000 g) and supernatant was removed. The *L. acidophilus* NCFM bacterial cells were washed once with differentiation medium and simple lipid micelles were prepared with the bacteria (see below).

The simple lipid micelles were prepared into 24 mM taurocholate (Sigma, St Louis, Mo., USA) in differentiation medium. The composition of simple micelles was: 0.6 mM oleic acid—2 mM taurocholate. One millilitre of micelles was prepared from oleic acid (6 µl of 100 mM stock) in a sterile glass tube. The oleic acid was dried under nitrogen gas at ambient temperature and the residue was dissolved in 83 µl of 24 mM taurocholate in differentiation medium and the volume was brought up to 1 ml either by bare differentiation medium, by differentiation medium consisting of 10% (v/v) MRS, or by differentiation medium consisting of *L. acidophilus* NCFM bacterial cells in a ratio of 50 bacterial cells to one Caco-2 cell.

The lipid micelles were applied at fifth day of Caco-2 differentiation on the apical side of the cells, and were left to react with the cells for 3 hours. As controls 10% (v/v) MRS medium and simple lipid micelles without *L. acidophilus* NCFM bacterial cells were used. They were prepared into differentiation medium.

After the treatments the cell culture media were aspirated and the cells were lysed with 150 µl of RA1 (Macherey-Nagel, Duren, Germany) supplemented with 1% (β-mercaptoethanol (Sigma). The RNA from the cell lysates was collected with Nucleospin 96 RNA isolation kit according to instruction provided by the manufacturer (Macherey-Nagel). The first-strand cDNA synthesis was done with random primers using Superscript III according to the instructions provided by the manufacturer (Invitrogen). The PYY expression pattern in the samples was analyzed using ABI PRISM Sequence Detection System (Applied Biosystems, Foster City, Calif., USA) using oligonucleotides specifically detecting homo sapiens PYY. The oligonucleotides included: forward primer: 5' GGA GGC CTC AGC TTG ACC 3 (SEQ ID NO: 1)'; reverse primer: 5' TGC GCA CGA ACA CCA TAG 3' (SEQ ID NO: 2); and the probe: Universal ProbeLibrary probe #10 (Roche). The obtained threshold cycle (Ct), which is the PCR-cycle at which the fluorescence intensity crosses a background threshold value, was transformed into absolute quantitative value by using a standard curve from quantified synthetic oligonucleotides representing the antisense sequence of the target transcript showing inverse log-linear relationship between the copy number and the PCR-cycle (Nurmi, J. T., Puolakkainen, P. A. & Rautonen, N. E. (2005) *Nutr Cancer* 51, 83-92).

The sequence of this standard oligonucleotide is: 5' TGC GCA CGA ACA CCA TAG CGA TAG CTT GTG AAG CAG ACG AGC AGG AGG TGG AAG GCG AGG GAA GTC CCA AGG GCT GCA CTG CCG CAG GTC AAG CTG AGG CCT CC 3' (SEQ ID NO: 3).

The statistical analysis was done with Student's t-test.

Results

Figure 4:
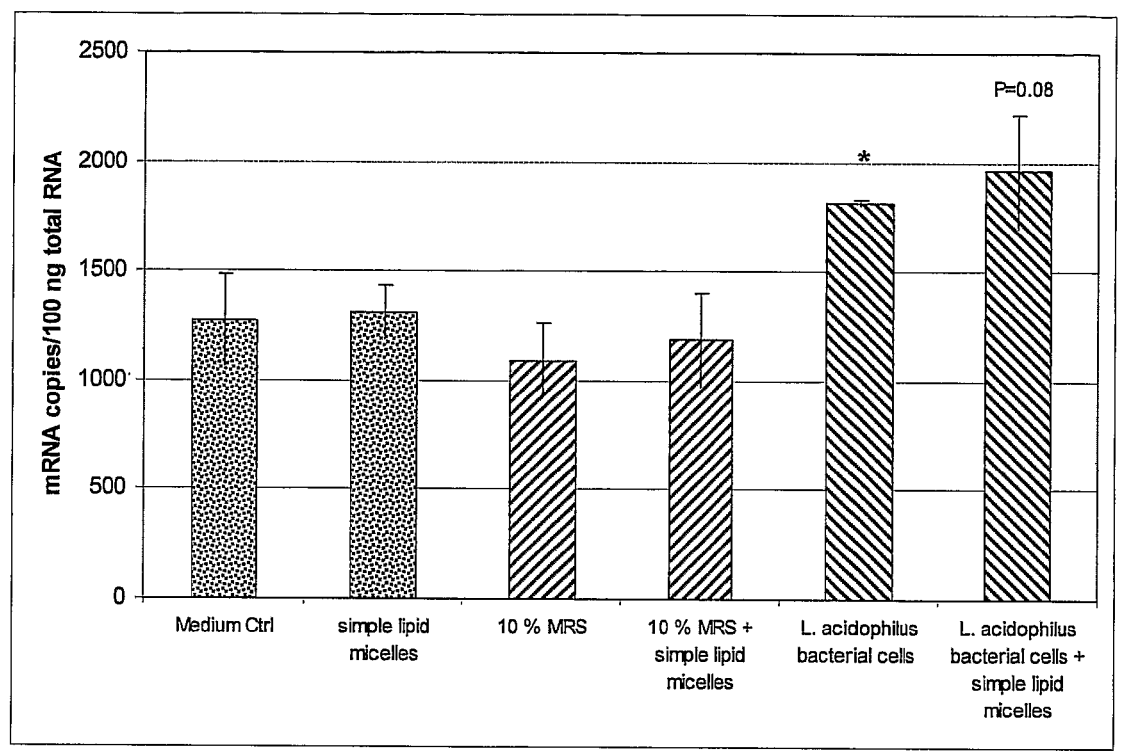
FIG. 4 shows the effect of *L. acidophilus* NCFM bacterial cells; simple lipid micelles and a combination thereof on PYY expression in differentiated Caco-2 cells.

The results are shown in FIG. 4.

The expression of satiety marker peptide YY (PYY) increased when Caco-2 cells were treated either with *L. acidophilus* NCFM bacterial cells alone or combined with the simple lipid micelles.

In the experiment with simple lipid micelles composed of 0.6 mM oleic acid in 2 mM taurocholate, the MRS broth combined with the simple lipid micelle mixture did not induce the PYY expression when compared with the treatment with lipid micelles alone. The *L. acidophilus* NCFM bacterial cells increased the expression of PYY compared to the controls (p<0.05 when compared to lipid micelles alone, and when compared to 10% MRS alone). When the lipid micelles were combined with the *L. acidophilus* NCFM bacterial cells in a ratio of 50 bacterial cells to one caco-2 cell the PYY expression was similarly induced although the high variation caused a decrease in the statistical significance (p=0.08 when compared to complex lipid micelle treatment).

EXAMPLE 7

Effect of *L. acidophilus* NCFM on PYY Expression (Time-Series)

Trial Outline

The experiment was done with Caco-2 cells which were differentiated according a 5-day protocol (Yamashita, S., Konishi, K., Yamazaki, Y., Taki, Y., Sakane, T., Sezaki, H. & Furuyama, Y. (2002) *J Pharm Sci* 91, 669-79). The cells were differentiated until the transepithelial electrical resistance (TEER) was over 200 ohm×cm$^2$. The cells were treated with bacterial cells (50 microbes: One Caco-2 cell) or with 0.1% (v/v), 1% (v/v), and 10% (v/v) cell-free supernatant diluted in caco-2 culture medium. The samples for PYY expression studies were collected at two different time points 3 h and 24 h after administering the test substances.

Materials & Methods

Caco-2 cells (HTB-37, American Type Culture Collection, ATCC) were maintained at 37° C. in humidified 5% $CO_2$ atmosphere in basal culture medium consisting of Dulbecco's Modified Eagle's Medium (DMEM, Invitrogen Carlsbad, Calif., US) supplemented with 20% FBS (Invitrogen), 2 mM stable glutamine (Invitrogen), 1× non-essential amino acids (Invitrogen), 20 U/ml penicillin (Invitrogen), 20 µg/ml streptomycin (Invitrogen), and 0.5 µg/ml amphotericin (Invitrogen).

The Caco-2 cells were used at passage 58 and plated as 6.6×10$^5$ cells/cm$^2$ on 12-well cell culture inserts (BIOCOAT HTS, BD Biosciences, Le Pont de Claix, France) and differentiated according to a 5-day protocol (Yamashita, S., Konishi, K., Yamazaki, Y., Taki, Y., Sakane, T., Sezaki, H. & Furuyama, Y. (2002) *J Pharm Sci* 91, 669-79). Briefly, after plating, the cells were incubated o/n at 37° C. at humidified 5% $CO_2$ atmosphere in basal cell culture medium without antibiotics after which the medium was aspirated and replaced with differentiation medium (Entero-STIM [BD Biosciences] supplemented with MITO+ serum extender [BD Biosciences], 250 µl/250 ml medium.) At 4th day of culture, the medium was replaced, and at $5^{th}$ day the experiment with bacteria as well as cell-free supernatant was conducted.

*L. acidophilus* NCFM (Danisco Cultures, Paris, France) was cultivated fresh in anaerobic conditions at 37° C. in Man, Rogosa and Sharpe (MRS) broth supplemented with 1.0% glucose (w/v) until the OD600 reached 1.0-1.5. The cell-free supernatant was collected by centrifugation (25° C., 5 min, 3000 g) and removed, and diluted 0.1% (v/v), 1% (v/v) and 10% (v/v) in differentiation medium, and filtered through 0.2 µm sterile syringe filter units (Sartorius, Goettingen, Germany). The bacterial cell density was estimated based on the OD-value, and they were washed once with EnteroStim and resuspended into EnteroStim in a ratio 50 bacterial cells to one Caco-2 cell. The test substances were applied onto the apical side of the Caco-2 cells.

After the treatments the cell culture media were aspirated and the cells were lysed with 150 µl of RA1 (Macherey-Nagel, Duren, Germany) supplemented with 1% β-mercaptoethanol (Sigma). The samples for PYY expression analysis from L. acidophilus NCFM samples were taken after 3 h and 24 h incubation. The RNA from the cell lysates was collected with Nucleospin 96 RNA isolation kit according to instruction provided by the manufacturer (Macherey-Nagel). The first-strand cDNA synthesis was done with random primers using Superscript III according to the instructions provided by the manufacturer (Invitrogen). The PYY expression pattern in the samples was analyzed using ABI PRISM Sequence Detection System (Applied Biosystems, Foster City, Calif., USA) using oligonucleotides specifically detecting homo sapiens PYY. The oligonucleotides included: forward primer: 5' GGA GGC CTC AGC TTG ACC 3' (SEQ ID NO: 1); reverse primer: 5' TGC GCA CGA ACA CCA TAG 3 (SEQ ID NO: 2)'; and the probe: Universal ProbeLibrary probe #10 (Roche). The obtained threshold cycle (Ct), which is the PCR-cycle at which the fluorescence intensity crosses a background threshold value, was transformed into absolute quantitative value by using a standard curve from quantified synthetic oligonucleotides representing the antisense sequence of the target transcript showing inverse log-linear relationship between the copy number and the PCR-cycle (Nurmi, J. T., Puolakkainen, P. A. & Rautonen, N. E. (2005) Nutr Cancer 51, 83-92). The sequence of this standard oligonucleotide is: 5' TGC GCA CGA ACA CCA TAG CGA TAG CTT GTG AAG CAG ACG AGC AGG AGG TGG AAG GCG AGG GAA GTC CCA AGG GCT GCA CTG CCG CAG GTC AAG CTG AGG CCT CC 3' (SEQ ID NO: 3).

The statistical analysis was done with ANOVA.

Results

Figure 6:
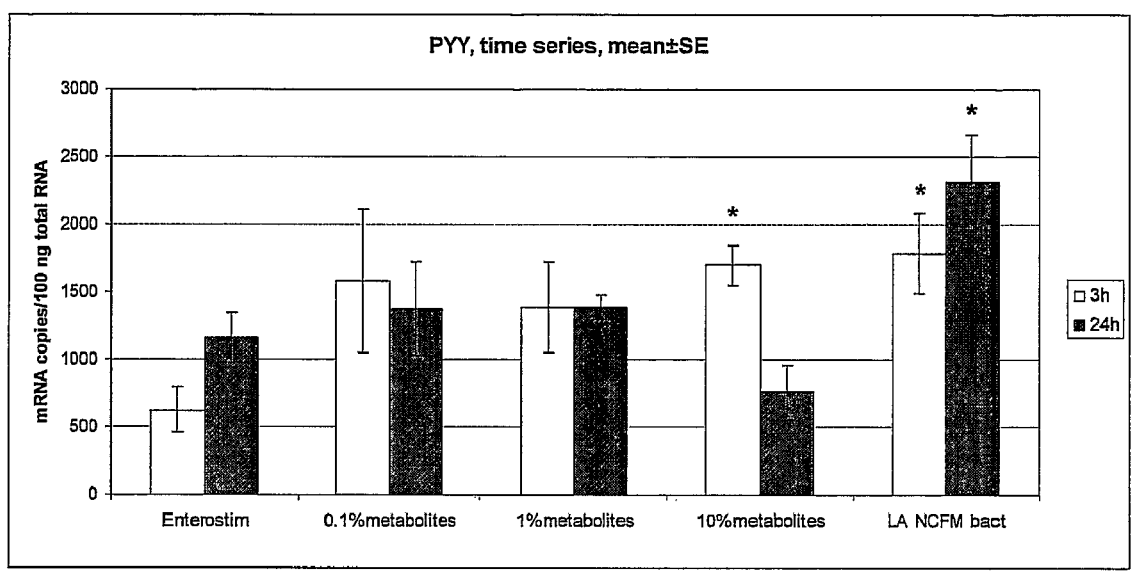
FIG. 6 shows the effect *L. acidophilus* NCFM cell-free supernatant and bacteria on PYY expression.

FIG. 6 shows the effect L. acidophilus NCFM cell-free supernatant and bacteria on PYY expression. Three different dilutions of cell-free supernatant 0.1 (v/v), 1% (v/v), and 10% (v/v) were used. The samples for PYY expression study were collected 3 and 24 hours after test substance application. *p<0.05 compared to Enterostim (medium) control; LA NCFM bact=L. acidophilus NCFM bacteria L. acidophilus NCFM bacterial cells increased the PYY expression at both time points, 3 h and 24 h after application of the bacteria Cell-free supernatant increased the PYY expression as 10% dilution after 3 h incubation.

The dose as well as the time of the treatment affects the PYY expression. The bacterial cells, particularly viable bacterial cells, may have a more sustainable effect on PYY expression than the metabolites.

EXAMPLE 8

Effect of L. curvatus 853 Bacterial Cells on PYY Expression

The experiment was done with Caco-2 cells which were differentiated according a 5-day protocol (Yamashita, S., Konishi, K., Yamazaki, Y., Taki, Y., Sakane, T., Sezaki, H. & Furuyama, Y. (2002) J Pharm Sci 91, 669-79). The cells were differentiated until the transepithelial electrical resistance (TEER) was over 200 ohm×cm². The cells were treated with L. curvatus 853 bacterial cells (50 microbes: One Caco-2 cell. The samples for gene expression analysis were collected after 4 hours of treatment.

Materials & Methods

Caco-2 cells (HTB-37, American Type Culture Collection, ATCC) were maintained at 37° C. in humidified 5% $CO_2$ atmosphere in basal culture medium consisting of Dulbecco's Modified Eagle's Medium (DMEM, Invitrogen Carlsbad, Calif., US) supplemented with 20% FBS (Invitrogen), 2 mM stable glutamine (Invitrogen), 1× non-essential amino acids (Invitrogen), 20 U/ml penicillin (Invitrogen), 20 µg/ml streptomycin (Invitrogen), and 0.5 µg/ml amphotericin (Invitrogen).

The Caco-2 cells were used at passage 58 and plated as $6.6 \times 10^5$ cells/cm² on 12-well cell culture inserts (BIOCOAT HTS, BD Biosciences, Le Pont de Claix, France) and differentiated according to a 5-day protocol (Yamashita, S., Konishi, K., Yamazaki, Y., Taki, Y., Sakane, T., Sezaki, H. & Furuyama, Y. (2002) J Pharm Sci 91, 669-79). Briefly, after plating, the cells were incubated o/n at 37° C. at humidified 5% $CO_2$ atmosphere in basal cell culture medium without antibiotics after which the medium was aspirated and replaced with differentiation medium (Entero-STIM [BD Biosciences] supplemented with MITO+ serum extender [BD Biosciences], 250 µl/250 ml medium.) At 4th day of culture, the medium was replaced, and at $5^{th}$ day the experiment with bacterial cells was conducted.

L. curvatus 853 was cultivated fresh in anaerobic conditions at 37° C. in Man, Rogosa and Sharpe (MRS) broth supplemented with 1.0% glucose until the OD600 reached 1.0-1.5. The cell-free supernatant was collected by centrifugation (25° C., 5 min, 3000 g) and removed. The bacterial cell density was estimated based on the OD-value, and they were washed once with EnteroStim, diluted and applied onto the apical side of the Caco-2 cells.

After the 4-hour treatment the cell culture media were aspirated and the cells were lysed with 150µl of RA1 (Macherey-Nagel, Duren, Germany) supplemented with 1% β-mercaptoethanol (Sigma). The RNA from the cell lysates was collected with Nucleospin 96 RNA isolation kit according to instruction provided by the manufacturer (Macherey-Nagel). The first-strand cDNA synthesis was done with random primers using Superscript III according to the instructions provided by the manufacturer (Invitrogen). The PYY expression pattern in the samples was analyzed using ABI PRISM Sequence Detection System (Applied Biosystems, Foster City, Calif., USA) using oligonucleotides specifically detecting homo sapiens PYY. The oligonucleotides included: forward primer: 5' GGA GGC CTC AGC TTG ACC 3' (SEQ ID NO: 1); reverse primer: 5' TGC GCA CGA ACA CCA TAG 3' (SEQ ID NO: 2); and the probe: Universal ProbeLibrary probe #10 (Roche). The obtained threshold cycle (Ct), which is the PCR-cycle at which the fluorescence intensity crosses a background threshold value, was transformed into absolute quantitative value by using a standard curve from quantified synthetic oligonucleotides representing the antisense sequence of the target transcript showing inverse log-linear relationship between the copy number and the PCR-cycle (Nurmi, J. T., Puolakkainen, P. A. & Rautonen, N. E. (2005) Nutr Cancer 51, 83-92). The sequence of this standard oligonucleotide is: 5' TGC GCA CGA ACA CCA TAG CGA TAG CTT GTG AAG CAG ACG AGC AGG AGG TGG AAG GCG AGG GAA GTC CCA AGG GCT GCA CTG CCG CAG GTC AAG CTG AGG CCT CC 3' (SEQ ID NO: 1).

The statistical analysis was done with ANOVA.

Results

Figure 7:
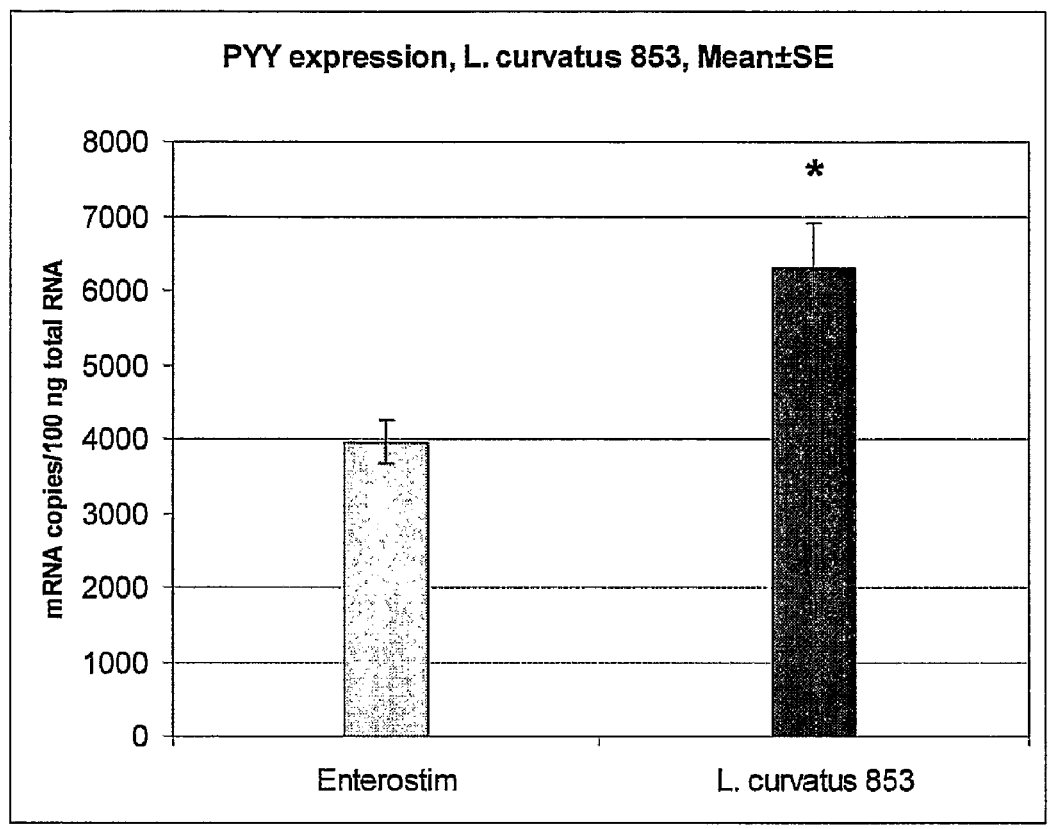
FIG. 7 shows the effect of *L. curvatus* 853 on PYY expression.

FIG. 7 shows the effect of *L. curvatus* 853 on PYY expression. The samples for PYY expression study were collected 4 hours after test substance application. *p<0.05 compared to medium only control.

*L. curvatus* 853 bacterial cells increased the PYY expression after 4 hours of incubation.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

References

Livak K J, and Schmittgen T D (2001) Analysis of relative gene expression data using real-time quantitative PCR and the 2(-Delta Delta C(T)) Method. Methods, 25(4): 402-8.

Yamashita S, Konishi K, Yamazaki Y, Taki Y, Sakane T, Sezani H, Furuyama Y (2002) New and better protocols for a short-term Caco-2 cell culture system. J Pharm Sci 91(3): 669-679.

The invention claimed is:

1. A method of modulating satiety signaling in a subject which method comprises administering to the subject an effective amount of at least one strain of a microorganism wherein the microorganism is selected from the group consisting of *Lactobacillus acidophilus* PTA-4797, *Bacillus lactis* 420, *Bacillus lactis* HN019 and *Lactobacillus salivarius* Ls-33, wherein one or more satiety marker levels are increased in plasma or gut, and wherein each satiety marker is selected from the group consisting of pancreatic polypeptide (PYY), cholecystokinin (CKK), Glucagon-like-peptide-1 (GLP-1), leptin, insulin and acetic acid.

2. The method of claim 1, wherein the microorganism modulates one or more other satiety markers.

3. The method of claim 1, wherein modulating satiety signaling occurs post-prandially.

4. The method of claim 1, wherein the satiety marker is selected from the group consisting ghrelin, orexin and leptin, and wherein leptin is obtained from brain.

5. The method of claim 1, wherein the microorganism is incorporated into a support.

6. The method of claim 1, wherein the support is a pharmaceutically acceptable support or a food product.

7. The method of claim 1, wherein the method is a cosmetic method of reducing excess weight in a non-obese subject.

8. The method of claim 6, wherein the support is a medicament.

9. The method of claim 1, wherein the method is a method of treating excess weight and/or a disease caused by excess weight.

SEQUENCE LISTING

```
<160> NUMBER OF SEQ ID NOS: 3

<210> SEQ ID NO 1
<211> LENGTH: 18
<212> TYPE: DNA
<213> ORGANISM: Artificial
<220> FEATURE:
<223> OTHER INFORMATION: Oligonucleotide primer

<400> SEQUENCE: 1
ggaggcctca gcttgacc                                                     18

<210> SEQ ID NO 2
<211> LENGTH: 18
<212> TYPE: DNA
<213> ORGANISM: Artificial
<220> FEATURE:
<223> OTHER INFORMATION: Oligonucleotide primer

<400> SEQUENCE: 2
tgcgcacgaa caccatag                                                     18

<210> SEQ ID NO 3
<211> LENGTH: 104
<212> TYPE: DNA
<213> ORGANISM: Artificial
<220> FEATURE:
<223> OTHER INFORMATION: Oligonucleotide

<400> SEQUENCE: 3
tgcgcacgaa caccatagcg atagcttgtg aagcagacga gcaggaggtg gaaggcgagg       60
gaagtcccaa gggctgcact gccgcaggtc aagctgaggc ctcc                       104
```

10. The method of claim 1, wherein the method is a method of treating obesity and/or a disease caused by obesity.

11. The method of claim 1, wherein the microorganism is a probiotic microorganism.

12. The method of claim 1, wherein the microorganism is a lactic acid bacterium.

13. The method of claim 1, wherein the microorganism is a probiotic lactic acid bacterium.

14. The method of claim 1, wherein the microorganism is administered in combination with a prebiotic.

15. The method of claim 14, wherein the prebiotic is one or more of the following inulin, a transgalacto-oligosaccharide, palantinoseoligosaccharide, soybean oligosaccharide, gentiooligosaccharide, oxylooligomers, non-degradable starch, lactosaccharose, lactulose, lactitol, maltitol, or polydextrose.

* * * * *